(12) United States Patent
Chen et al.

(10) Patent No.: US 11,058,791 B2
(45) Date of Patent: Jul. 13, 2021

(54) THIN NANOCOMPOSITE FILM FOR USE IN AN ABSORBENT ARTICLE

(71) Applicant: Kimberly-Clark Worldwide, Inc., Neenah, WI (US)

(72) Inventors: Feng Chen, Neenah, WI (US); James Hongxue Wang, Shanghai (CN); Gregory J. Wideman, Menasha, WI (US); Michael J. Faulks, Neenah, WI (US); Mark M. Mleziva, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 737 days.

(21) Appl. No.: 15/107,600

(22) PCT Filed: Jan. 30, 2015

(86) PCT No.: PCT/US2015/013838
§ 371 (c)(1),
(2) Date: Jun. 23, 2016

(87) PCT Pub. No.: WO2015/116965
PCT Pub. Date: Aug. 6, 2015

(65) Prior Publication Data
US 2016/0325007 A1 Nov. 10, 2016

Related U.S. Application Data

(60) Provisional application No. 61/934,453, filed on Jan. 31, 2014.

(51) Int. Cl.
*A61F 13/514* (2006.01)
*B32B 27/18* (2006.01)
(Continued)

(52) U.S. Cl.
CPC ........ *A61L 15/42* (2013.01); *A61F 13/15642* (2013.01); *A61F 13/51401* (2013.01);
(Continued)

(58) Field of Classification Search
CPC .......... A61F 13/51401; A61F 13/51456; A61F 13/5148; A61F 2013/51038;
(Continued)

(56) References Cited

U.S. PATENT DOCUMENTS 3,354,506 A 11/1967 Raley
3,650,649 A 3/1972 Schippers
(Continued)

FOREIGN PATENT DOCUMENTS

CN 1389501 1/2003
RU 2007134346 A 3/2007
(Continued)

OTHER PUBLICATIONS

Russian Search Report dated Sep. 7, 2017, 2 pages.
(Continued)

*Primary Examiner* — Catharine L Anderson
(74) *Attorney, Agent, or Firm* — Dority & Manning, P.A.

(57) ABSTRACT

A thin nanocomposite film for use in an absorbent article is provided. The film contains an ethylene polymer, a nanoclay having an organic surface treatment, and a compatibilizer that includes an olefin polymer containing an ethylenically unsaturated carboxylic acid monomer. The present inventors have discovered that through selective control over the particular type and concentration of the components used to form the film, as well as the manner in which it is formed, the modulus and tensile strength of the film can be significantly improved without having an adverse impact on its ductility.

26 Claims, 11 Drawing Sheets

(51) Int. Cl.
  *B32B 27/20* (2006.01)
  *A61L 15/42* (2006.01)
  *B32B 27/12* (2006.01)
  *B32B 27/32* (2006.01)
  *B32B 5/02* (2006.01)
  *B32B 7/03* (2019.01)
  *A61F 13/15* (2006.01)
  *A61L 15/18* (2006.01)
  *A61L 15/24* (2006.01)
  *A61F 13/51* (2006.01)

(52) U.S. Cl.
  CPC ........ *A61F 13/51456* (2013.01); *A61L 15/18* (2013.01); *A61L 15/24* (2013.01); *B32B 5/022* (2013.01); *B32B 7/03* (2019.01); *B32B 27/12* (2013.01); *B32B 27/18* (2013.01); *B32B 27/20* (2013.01); *B32B 27/32* (2013.01); *A61F 2013/51023* (2013.01); *A61F 2013/51038* (2013.01); *A61F 2013/51409* (2013.01); *A61F 2013/51472* (2013.01); *B32B 2250/03* (2013.01); *B32B 2262/0238* (2013.01); *B32B 2262/0246* (2013.01); *B32B 2262/0253* (2013.01); *B32B 2262/0261* (2013.01); *B32B 2262/0276* (2013.01); *B32B 2264/10* (2013.01); *B32B 2264/102* (2013.01); *B32B 2270/00* (2013.01); *B32B 2307/514* (2013.01); *B32B 2307/54* (2013.01); *B32B 2307/726* (2013.01); *B32B 2307/7244* (2013.01); *B32B 2307/7265* (2013.01); *B32B 2307/732* (2013.01); *B32B 2555/02* (2013.01)

(58) Field of Classification Search
  CPC .... A61F 2013/5105; A61F 2013/51057; A61F 2013/51409; A61F 2013/51472; B32B 7/03; B32B 27/18; B32B 27/20; B32B 27/205; B32B 2262/105; B32B 2264/107
  See application file for complete search history.

(56) References Cited

U.S. PATENT DOCUMENTS

| | | |
|---|---|---|
| 3,801,429 A | 4/1974 | Schrenk et al. |
| 4,041,203 A | 8/1977 | Brock et al. |
| 4,374,888 A | 2/1983 | Bornslaeger |
| 4,704,116 A | 11/1987 | Enloe |
| 4,728,325 A | 3/1988 | Spiller |
| 4,766,029 A | 8/1988 | Brock et al. |
| 4,789,699 A | 12/1988 | Kieffer et al. |
| 4,798,603 A | 1/1989 | Meyer et al. |
| 4,886,512 A | 12/1989 | Damico et al. |
| 4,897,449 A | 1/1990 | Gaillard et al. |
| 5,102,948 A | 4/1992 | Deguchi et al. |
| 5,169,706 A | 12/1992 | Collier, IV et al. |
| 5,192,606 A | 3/1993 | Proxmire et al. |
| 5,213,881 A | 5/1993 | Timmons et al. |
| 5,248,309 A | 9/1993 | Serbiak et al. |
| 5,254,111 A | 10/1993 | Cancio et al. |
| 5,272,236 A | 12/1993 | Lai et al. |
| 5,322,728 A | 6/1994 | Davey et al. |
| 5,464,688 A | 11/1995 | Timmons et al. |
| 5,472,775 A | 12/1995 | Obijeski et al. |
| 5,486,166 A | 1/1996 | Bishop et al. |
| 5,490,846 A | 2/1996 | Ellis et al. |
| 5,558,659 A | 9/1996 | Sherrod et al. |
| 5,571,619 A | 11/1996 | McAlpin et al. |
| 5,649,916 A | 7/1997 | DiPalma et al. |
| 5,695,868 A | 12/1997 | McCormack |
| 5,702,377 A | 12/1997 | Collier, IV et al. |
| 5,853,886 A | 12/1998 | Pinnavaia et al. |
| 5,877,248 A | 3/1999 | Beall et al. |
| 5,880,197 A | 3/1999 | Beall et al. |
| 5,931,823 A | 8/1999 | Stokes et al. |
| 6,060,638 A | 5/2000 | Paul et al. |
| 6,090,325 A | 7/2000 | Wheat et al. |
| 6,110,158 A | 8/2000 | Kielpikowski |
| 6,150,002 A | 11/2000 | Varona |
| 6,380,445 B1 | 4/2002 | Rietz et al. |
| 6,455,161 B1 | 9/2002 | Regnier et al. |
| 6,462,122 B1 | 10/2002 | Qian et al. |
| 6,511,465 B1 | 1/2003 | Freiburger et al. |
| 6,583,209 B2 | 6/2003 | Mehta et al. |
| 6,632,868 B2 | 10/2003 | Qian et al. |
| 6,663,611 B2 | 12/2003 | Blaney et al. |
| 6,716,203 B2 | 4/2004 | Sorebo et al. |
| 6,770,697 B2 | 8/2004 | Drewniak et al. |
| 6,812,272 B2 | 11/2004 | Fischer |
| 6,824,734 B2 | 11/2004 | Boggs et al. |
| 6,838,508 B2 | 1/2005 | Hsiao et al. |
| 6,844,389 B2 | 1/2005 | Mehta et al. |
| 6,846,532 B1 | 1/2005 | Bensur |
| 6,869,985 B2 | 3/2005 | Mohanty et al. |
| 6,888,044 B2 | 5/2005 | Fell et al. |
| 7,029,735 B2 | 4/2006 | Flat et al. |
| 7,030,188 B2 | 4/2006 | Botros et al. |
| 7,060,867 B2 | 6/2006 | Jameson |
| 7,138,452 B2 | 11/2006 | Kim et al. |
| 7,553,898 B2 | 6/2009 | Rafailovich et al. |
| 7,579,413 B2 | 8/2009 | Mohanty et al. |
| 7,658,989 B2 | 2/2010 | DeSimone et al. |
| 7,678,444 B2 | 3/2010 | Tedford, Jr. et al. |
| 7,758,557 B2 | 7/2010 | Faulks et al. |
| 7,837,899 B2 | 11/2010 | Moad et al. |
| 7,868,080 B2 | 1/2011 | Kim et al. |
| 7,872,169 B2 | 1/2011 | Ruiz et al. |
| 7,888,419 B2 | 2/2011 | Cooper et al. |
| 8,124,678 B2 | 2/2012 | Boscia et al. |
| 8,198,200 B2 | 6/2012 | Autran et al. |
| 8,283,415 B2 | 10/2012 | Brusson et al. |
| 8,323,258 B2 | 12/2012 | Dalal et al. |
| 8,445,595 B2 | 5/2013 | Radermacher et al. |
| 8,471,533 B2 | 6/2013 | Hussain et al. |
| 8,518,313 B2 | 8/2013 | Szekely |
| 8,518,318 B2 | 8/2013 | Jacobs |
| 8,722,804 B2 | 5/2014 | Lue et al. |
| 8,906,488 B2 | 12/2014 | Lee et al. |
| 8,907,935 B2 | 12/2014 | Syed et al. |
| 8,940,815 B2 | 1/2015 | Debras et al. |
| 9,012,534 B2 | 4/2015 | Debras et al. |
| 2003/0116462 A1 | 6/2003 | Sorebo et al. |
| 2004/0060112 A1 | 4/2004 | Fell et al. |
| 2004/0078015 A1 | 4/2004 | Copat et al. |
| 2005/0054255 A1 | 3/2005 | Morman et al. |
| 2005/0059941 A1 | 3/2005 | Baldwin et al. |
| 2005/0245162 A1 | 11/2005 | McCormack et al. |
| 2006/0094810 A1 | 5/2006 | Kim et al. |
| 2006/0122311 A1 | 6/2006 | Kim et al. |
| 2006/0122312 A1 | 6/2006 | Kim et al. |
| 2006/0155018 A1 | 7/2006 | Metzemacher et al. |
| 2006/0276579 A1 | 12/2006 | Jarus et al. |
| 2007/0043155 A1 | 2/2007 | Pees |
| 2007/0254142 A1 | 11/2007 | Collias et al. |
| 2007/0264897 A1 | 11/2007 | Collias et al. |
| 2008/0033093 A1 | 2/2008 | Menceloglu et al. |
| 2009/0292055 A1 | 11/2009 | Jarus et al. |
| 2010/0092793 A1 | 4/2010 | Aithani et al. |
| 2010/0121295 A1 | 5/2010 | Collias et al. |
| 2010/0159203 A1* | 6/2010 | Shi ................ A61L 15/225 428/159 |
| 2010/0178477 A1 | 7/2010 | Jacobs |
| 2010/0304068 A1 | 12/2010 | Ferrara et al. |
| 2011/0028633 A1 | 2/2011 | Moad et al. |
| 2011/0052847 A1 | 3/2011 | Roberts et al. |
| 2011/0220851 A1 | 9/2011 | Sue et al. |
| 2011/0263776 A1 | 10/2011 | Debras et al. |
| 2012/0039975 A1 | 2/2012 | Lagaron Cabello et al. |
| 2012/0238682 A1 | 9/2012 | Yang et al. |
| 2012/0315454 A1 | 10/2012 | De La Bruniere |
| 2012/0321856 A1 | 12/2012 | Afshari |

(56) References Cited

U.S. PATENT DOCUMENTS

| | | |
|---|---|---|
| 2012/0328841 A1 | 12/2012 | Afshari |
| 2013/0225707 A1 | 8/2013 | Radermacher et al. |

FOREIGN PATENT DOCUMENTS

| | | |
|---|---|---|
| RU | 2009123011 A | 12/2010 |
| WO | WO 2007/121048 A1 | 10/2007 |
| WO | WO2015/116953 | 8/2015 |
| WO | WO2015/116958 | 8/2015 |

OTHER PUBLICATIONS

Article—Achaby et al., "Processing and Properties of Polyethylene Reinforced by Graphene Nanosheets and Carbon Nanotubes," *Materials and Design*, vol. 44, 2013, pp. 81-89.

Article—Borah et al., "Effect of Organoclay Platelets on Morphology and Properties of LLDPE/EMA Blends," *Materials Science and Engineering A*, vol. 528, 2011, pp. 2820-2830.

Article—Drozdov et al., "Viscoelasticity of Polyethylene/Montmorillonite Nanocomposite Melts," *Computational Materials Science*, vol. 43, 2008, pp. 1027-1035.

Article—Green et al., "Structure Property Relationships in Polyethylene/Montmorillonite Nanodielectrics," *IEEE Transactions on Dielectric and Electrical Insulation*, vol. 15, No. 1, Feb. 2008, pp. 134-143.

Article—Hershkovits-Mezuman et al., "The Effects of Interfacial Interactions on Lamellar Morphologies in Thin and Ultrathin Films and Nanocomposites of LLDPE," *Composites: Part A*, vol. 41, 2010, pp. 1066-1071.

Article—Hetzer et al., "Influence of compatibiliser blends on mechanical and thermal properties of polymer-clay nanocomposites," *Materials Science and Technology*, vol. 27, No. 1, Jan. 2011, pp. 663-688.

Article—Kamal et al., "Surface Energy of Modified Nanoclays and Its Effect on Polymer/Clay Nanocomposites," *Journal of Adhesion Science and Technology*, vol. 23, 2009, pp. 663-688.

Product Information—DOW™ HDPE DMDA-8007 NT 7, 3 pages.

International Search Report and Written Opinion for PCT/US2015/013838, dated May 15, 2015, 17 pages.

\* cited by examiner

THIN NANOCOMPOSITE FILM FOR USE IN AN ABSORBENT ARTICLE

RELATED APPLICATION

The present application is the national stage entry International Patent Application No. PCT/US2015/013838 having a filing date of Jan. 30, 2015, which claims priority to U.S. Patent Application Serial No. 61/934,453 filed on Jan. 31, 2014, which are incorporated herein in their entirety by reference thereto.

BACKGROUND OF THE INVENTION

Absorbent articles, such as diapers, are generally constructed from an absorbent core that is positioned between a liquid-permeable topsheet, which defines a "body-facing" surface disposed toward the body, and a liquid-impermeable backsheet, which defines a "garment-facing" surface disposed away from the body. The backsheet is often formed from a polypropylene nonwoven web that is laminated to a film made from linear low density polyethylene ("LLDPE"). One of the problems with these conventional backsheets, however, is that conventional films often lack good impact strength and stiffness. While attempts have been made to add various fillers to the film to improve these properties, this usually results in a corresponding decrease in ductility, which is highly undesirable. As such, a need currently exists for a film for use in an absorbent article that can exhibit good strength properties without a substantial reduction in ductility.

SUMMARY OF THE INVENTION

In accordance with one embodiment of the present invention, an absorbent article is disclosed that comprises a liquid permeable layer, a generally liquid-impermeable layer, and an absorbent core positioned between the liquid permeable layer and the generally liquid-impermeable layer. The generally liquid-impermeable layer contains a film having a thickness of about 50 micrometers or less. The film contains a layer that is formed from a polymer composition, the polymer composition containing an ethylene polymer, nanoclay having an organic surface treatment, and polyolefin compatibilizer that contains an olefin component and a polar component.

In accordance with another embodiment of the present invention, a film is disclosed that has a thickness of about 50 micrometers or less. The film contains a layer that is formed from a polymer composition, the polymer composition containing from about 75 wt. % to about 99 wt. % of an α-olefin/ethylene copolymer, from about 0.5 wt. % to about 20 wt. % of a nanoclay having an organic surface treatment, and from about 0.1 wt. % to about 10 wt. % of a polyolefin compatibilizer that contains an olefin component and a polar component. The film exhibits a peak elongation of about 450% or more in the machine direction and an ultimate tensile strength of from about 20 to about 150 MPa in the machine direction.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
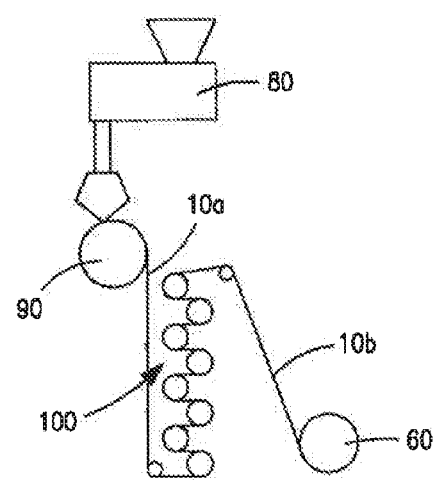
FIG. 1 is a schematic illustration of one embodiment of a process that can be used to form the film of the present invention.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a thin nanocomposite film for use in an absorbent article (e.g., backsheet). The film contains an ethylene polymer, a nanoclay having an organic surface treatment, and a polyolefin compatibilizer that includes an olefin component and a polar component. Ethylene polymers, for instance, typically constitute from about 80 wt. % to about 99.9 wt. %, in some embodiments from about 90 wt. % to about 99.5 wt. %, and in some embodiments, from about 95 wt. % to 98 wt. % of the polymer content of the polymer composition. Likewise, the ethylene polymers may constitute from about 75 wt. % to about 99 wt. %, in some embodiments from about 80 wt. % to about 98 wt. %, and in some embodiments, from about 85 wt. % to 95 wt. % of the entire polymer composition. Nanoclays may likewise constitute from about 0.5 wt. % to about 20 wt. %, in some embodiments from about 1 wt. % to about 10 wt. %, and in some embodiments, from about 2 wt. % to about 8 wt. % of the polymer composition, while compatibilizers may constitute from about 0.1 wt. % to about 10 wt. %, in some embodiments from about 0.2 wt. % to about 8 wt. %, and in some embodiments, from about 0.5 wt. % to about 5 wt. % of the polymer composition.

The present inventors have discovered that through selective control over the particular type and concentration of the components used to form the film, as well as the manner in which it is formed, the modulus and tensile strength of the film can be significantly improved without having an adverse impact on its ductility. For example, without intending to be limited by theory, it is believed that the organic surface treatment can have a plastifying-like effect on the nanoclay, which can reduce the degree of surface friction between the nanoclay and domains of the ethylene polymer when the composition is subjected to an elongational force. It is also believed that the surface treatment can have a lubricating effect, which allows the macromolecular chains of the ethylene polymer to slip along the nanoclay surface without causing debonding, thus maintaining a high degree of ductility. This can be accomplished by selectively controlling the particular type of surface treatment, the type of ethylene polymer, and the degree of mixing during melt extrusion. Furthermore, the nanoclay can optionally be pre-blended with the ethylene polymer and compatibilizer to form the polymer composition, which is thereafter passed through an extrusion die and formed into a film. Through such a multi-step formation process, the nanoclay can become well-dispersed and more uniformly oriented, thereby even further enhancing ductility. It is believed that certain types of formation processes (e.g., cast film or blown film processes) are also particularly well suited to allow the formation of unique structures with a high degree of ductility.

One parameter that is indicative of good ductility is the peak elongation of the film in the machine direction ("MD") and/or cross-machine direction ("CD"). For example, the film typically exhibits a peak elongation in the machine direction of about 400% or more, in some embodiments about 500% or more, in some embodiments about 550% or more, and in some embodiments, from about 600% to about 2000%. The film may likewise exhibit a peak elongation in the cross-machine direction of about 750% or more, in some embodiments about 800% or more, in some embodiments about 800% or more, and in some embodiments, from about 850% to about 2500%. Despite having such good ductility, the film of the present invention is nevertheless able to retain good mechanical strength. For example, the film of the present invention may exhibit an ultimate tensile strength in the machine direction and/or cross-machine direction of from about 20 to about 150 Megapascals (MPa), in some embodiments from about 25 to about 100 MPa, and in some embodiments, from about 30 to about 80 MPa. The Young's modulus of elasticity of the film, which is equal to the ratio of the tensile stress to the tensile strain and is determined from the slope of a stress-strain curve, may also be good. For example, the film typically exhibits a Young's modulus in the machine direction and/or cross-machine direction of from about 50 to about 500 MPa, in some embodiments from about 100 to about 400 MPa, and in some embodiments, from about 150 to about 350 MPa.

Surprisingly, the good ductility and other mechanical properties can be achieved even though the film has a very low thickness. In this regard, the normalized mechanical properties, which are determined by dividing a particular mechanical value (e.g., Young's modulus, tensile strength, or peak elongation) by the average film thickness (μm), may also be improved. For example, the film may exhibit a normalized peak elongation in the machine direction of about 30%/μm or more, in some embodiments about 40%/μm or more, and in some embodiments, from about 50%/μm to about 150%/μm. The film may likewise exhibit a normalized peak elongation in the cross-machine direction of about 40%/μm or more, in some embodiments about 50%/μm or more, and in some embodiments, from about 60%/μm to about 200%/μm. The film may exhibit a normalized ultimate tensile strength in the machine direction and/or cross-machine direction of from about 0.5 to about 20 MPa/μm, in some embodiments from about 1 to about 12 MPa/μm, and in some embodiments, from about 2 to about 8 MPa/μm. The normalized Young's modulus in the machine direction and/or cross-machine direction may also be from about 5 to about 50 MPa/μm, in some embodiments from about 10 to about 40 MPa/μm, and in some embodiments, from about 15 to about 35 MPa/μm. The actual thickness of the film is typically about 50 micrometers or less, in some embodiments from about 1 to about 40 micrometers, in some embodiments from about 5 to about 35 micrometers, and in some embodiments, from about 10 to about 30 micrometers.

The present inventors have also discovered that the film may generate a relatively low degree of noise when physically deformed. When subjected to physical deformation for two (2) minutes, for instance, the noise level of the film may be about 45 decibels (dB) or less, in some embodiments about 42 dB or less, and in some embodiments, from about 20 dB to about 40 dB, such as determined at a frequency of 2,000 Hz or 4,000 Hz. The "normalized noise level" of the film, which is determined by dividing the noise level of the film that is generated while the film is subjected to physical deformation for two (2) minutes by the noise level generated by an ambient environment, may likewise be about 2.5 or less, in some embodiments about 2.4 or less, and in some embodiments, from about 1.5 to about 2.3, such as determined at a frequency of 2,000 Hz or 4,000 Hz. The entire absorbent article may also exhibit a relatively low degree of noise. For instance, when subjected to physical deformation for two (2) minutes, the noise level generated by the absorbent article may be about 30 decibels (dB) or less, in some embodiments about 29 dB or less, and in some embodiments, from about 20 dB to about 28 dB, as determined at a frequency of 2000 Hz. The "normalized noise level" of the absorbent article may likewise be about 1.55 or less, in some embodiments about 1.50 or less, and in some embodiments, from about 0.5 to about 1.45, such as determined at a frequency of 2,000 Hz or 4,000 Hz.

In addition to a reduced noise level, the film of the present invention may also have excellent barrier properties to oxygen transmission. Without intending to be limited by theory, it is believed that the nanoclay platelet structure can create a tortuous pathway in the film, which may slow down the transmission rate and reduce the amount of permeant oxygen. For example, the oxygen transmission rate may be about 350 cm$^3$/100 in$^2$*24-hours or less, in some embodiments about 330 cm$^3$/100 hours or less, and in some embodiments, from about 100 to about 300 cm$^3$/100 in$^2$*24-hours, such as determined in accordance with ASTM D3985-05 at a temperature of 23° C. and a relative humidity of 0%.

Various embodiments of the present invention will now be described in more detail.

I. Polymer Composition

A. Ethylene Polymer

Any of a variety of ethylene polymers may generally be employed in the present invention. In one embodiment, for instance, the ethylene polymer may be a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %. The density of the polyethylene may vary depending on the type of polymer employed, but generally ranges from about 0.85 to about 0.96 grams per cubic centimeter (g/cm$^3$). Polyethylene "plastomers", for instance, may have a density in the range of from about 0.85 to about 0.91 g/cm$^3$. Likewise, "linear low density polyethylene" (LLDPE) may have a density in the range of from about 0.91 to about 0.940 g/cm$^3$; "low density polyethylene" (LDPE) may have a density in the range of from about 0.910 to about 0.940 g/cm$^3$; and "high density polyethylene" (HDPE) may have density in the range of from about 0.940 to about 0.960 g/cm$^3$, such as determined in accordance with ASTM D792.

In certain embodiments, an ethylene polymer may be employed that has a relatively low density in the range of about 0.94 g/cm$^3$ or less, in some embodiments from about 0.85 to about 0.94 g/cm$^3$, and in some embodiments, from about 0.90 to about 0.935 g/cm$^3$. One or more polymers may be employed in the composition that has these density characteristics. Linear low density polyethylene ("LLDPE") and/or low density polyethylene ("LDPE") are particularly suitable. The low density ethylene polymer may have a relatively low melting temperature and modulus of elasticity, which can provide the resulting film with a relatively soft and ductile feel. For example, the low density ethylene polymer may have a melting temperature of from about 50° C. to about 145° C., in some embodiments from about 75° C. to about 140° C., and in some embodiments, from about 100° C. to about 135° C., and a modulus of elasticity of from about 50 to about 700 MPa, in some embodiments from about 75 to about 600 MPa, and in some embodiments, from about 100 to about 500 MPa, as determined in accordance with ASTM D638-10. The low density ethylene polymer may also have a melt flow index of from about 0.1 to about 100 grams per 10 minutes, in some embodiments from about 0.5 to about 50 grams per 10 minutes, and in some embodiments, from about 1 to about 40 grams per 10 minutes, determined at a load of 2160 grams and at 190° C., as determined in accordance with ASTM D1238-13 (or ISO 1133).

If desired, low density ethylene polymers may constitute a substantial majority of the polymers employed in the composition. For example, low density ethylene polymers may constitute about 80 wt. % or more, in some embodiments about 85 wt. % or more, and in some embodiments, from about 90 wt. % to 100 wt. % of the polymers employed in the composition. Of course, in other embodiments, high density ethylene polymers may also be employed. For example, low density ethylene polymers may constitute from about 5 wt. % to about 90 wt. %, in some embodiments from about 10 wt. % to about 80 wt. %, and in some embodiments, from about 20 wt. % to 70 wt. % of the polymer composition and high density ethylene polymers may constitute from about 5 wt. % to about 90 wt. %, in some embodiments from about 10 wt. % to about 80 wt. %, and in some embodiments, from about 20 wt. % to 70 wt. % of the polymer composition. The high density ethylene polymers typically have a density of greater than about 0.94 g/cm$^3$, in some embodiments from about 0.945 to about 0.98 g/cm$^3$, and in some embodiments, from about 0.95 to about 0.97 g/cm$^3$. Once again, one or more polymers may be employed in the composition that has these characteristics. High density polyethylene ("HDPE") is particularly suitable. The high density ethylene polymers may have a relatively low melting temperature and high modulus of elasticity. For example, the high density ethylene polymers may have a melting temperature of from about 70° C. to about 160° C., in some embodiments from about 85° C. to about 150° C., and in some embodiments, from about 110° C. to about 145° C., and a modulus of elasticity of from about 700 to about 5,000 MPa, in some embodiments from about 750 to about 3,000 MPa, and in some embodiments, from about 1,000 to about 2,000 MPa, as determined in accordance with ASTM D638-10. The high density ethylene polymers may also have a melt flow index of from about 0.1 to about 100 grams per 10 minutes, in some embodiments from about 0.5 to about 50 grams per 10 minutes, and in some embodiments, from about 1 to about 40 grams per 10 minutes, determined at a load of 2160 grams and at 190° C., as determined in accordance with ASTM D1238-13 (or ISO 1133).

Various known techniques may generally be employed to form ethylene polymers. For instance, ethylene polymers may be formed using a free radical or a coordination catalyst (e.g., Ziegler-Natta). Typically, the ethylene polymer is formed from multi-site Ziegler-Natta catalysts, the resulting ethylene polymer has a broad molecular weight distribution with a polydispersity index (weight average molecular weight divided by number average molecular weight) of up to 20 or higher. The ethylene polymer made by a single-site coordination catalyst, such as a metallocene catalyst, has a narrow molecular weight distribution. Such a catalyst system produces ethylene polymers in which a comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et al. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyOzirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

B. Nanoclay

The term "nanoclay" generally refers to nanoparticles of a clay material (a naturally occurring mineral, an organically modified mineral, or a synthetic nanomaterial). The clay material typically has a flake-like morphology in that it possesses a relatively flat or platelet shape. The clay platelets may, for example, have an average thickness of from about 0.2 to about 100 nanometers, in some embodiments from about 0.5 to about 50 nanometers, and in some embodiments, from about 1 to about 20 nanometers. The "aspect ratio" of the clay material (i.e., the average length of the platelets divided by the average thickness) is also relatively large, such as from about 20 to about 1000, in some embodiments from about 50 to about 80, in some embodiments, from about 100 to about 400. The average length (e.g., diameter) may, for instance, range from about 20 nanometers to about 10 micrometers, in some embodiments from about 100 nanometers to about 5 micrometers, and in some embodiments, from about 200 nanometers to about 4 micrometers.

The clay material may be formed from a phyllosilicate, such as a smectite clay mineral (e.g., bentonite, kaolinite, or montmorillonite, as well as salts thereof, such as sodium montmorillonite, magnesium montmorillonite, calcium montmorillonite, etc.); nontronite; beidellite; volkonskoite; hectorite; saponite; sauconite; sobockite; stevensite; svinfordite; vermiculite; etc. Other useful nanoclays include micaceous minerals (e.g., illite) and mixed illite/smectite minerals, such as rectorite, tarosovite, ledikite and admixtures of illites with the clay minerals named above. Particularly suitable are montmorillonite (2:1 layered smectite clay structure), bentonite (aluminium phyllosilicate formed primarily of montmorillonite), kaolinite (1:1 aluminosilicate having a platy structure and empirical formula of $Al_2Si_2O_5(OH)_4$), halloysite (1:1 aluminosilicate having a tubular structure and empirical formula of $Al_2Si_2O_5(OH)_4$), etc.

As noted above, the nanoclay also contains an organic surface treatment that enhances the hydrophobicity of the clay material and thus improves its compatibility with the ethylene polymer. In one embodiment, the organic surface treatment may be formed from a quaternary onium (e.g., salt or ion), which may become intercalated via ion-exchange into the interlayer spaces between adjacent layered clay platelets. The quaternary onium ion may have the following structure:

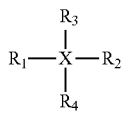

wherein

X is N, P, S, or O; and $R_1$, $R_2$, $R_3$ and $R_4$ are independently hydrogen or organic moieties, such as linear or branched alkyl, aryl or aralkyl moieties having 1 to about 24 carbon atoms.

Particularly suitable quaternary ammonium ions are those having the structure below:

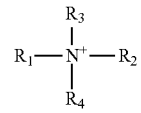

wherein $R_1$ is a long chain alkyl moiety ranging from $C_6$ to $C_{24}$, straight or branched chain, including mixtures of long chain moieties, such as $C_6$, $C_8$, $C_{10}$, $C_{12}$, $C_{14}$, $C_{16}$, $C_{18}$, $C_{20}$, $C_{22}$ and $C_{24}$, alone or in any combination; and $R_2$, $R_3$ and $R_4$ are moieties, which may be the same or different, selected from the group consisting of H, alkyl, hydroxyalkyl, benzyl, substituted benzyl, e.g., straight or branched chain alkyl-substituted and halogen-substituted; ethoxylated or propoxylated alkyl; ethoxylated or propoxylated benzyl (e.g., 1-10 moles of ethoxylation or 1-10 moles of propoxylation).

Additional useful multi-charged spacing/coupling agents include for example, tetra-, tri-, and di-onium species such as tetra-ammonium, tri-ammonium, and di-ammonium (primary, secondary, tertiary, and quaternary), -phosphonium, -oxonium, or -sulfonium derivatives of aliphatic, aromatic or arylaliphatic amines, phosphines, esters, alcohols and sulfides. Illustrative of such materials are di-onium compounds of the formula:

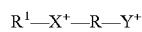

where $X^+$ and $Y^+$, are the same or different, and are ammonium, sulfonium, phosphonium, or oxonium radicals such as —$NH(CH_3)_2^+$, —$NH_2(CH_3)^+$, —$N(CH_3)_3^+$, —$N(CH_3)_2(CH_2CH_3)^+$, —$N(CH_3)(CH_2CH_3)_2^+$, —$S(CH_3)_2^+$, —$S(CH_3)_2^+$, —$P(CH_3)_3^+$, —$NH_3^+$, etc.;

R is an organic spacing, backbone radical, straight or branched, such as those having from 2 to 24 carbon atoms, and in some embodiments from 3 to 10 carbon atoms, in a backbone organic spacing molecule covalently bonded at its ends to charged $N^+$, $P^+$, $S^+$ and/or $O^+$ cations;

$R^1$ can be hydrogen, or a linear or branched alkyl radical of 1 to 22 carbon atoms, linear or branched, and in some embodiments, 6 to 22 carbon atoms.

Illustrative of useful R groups are alkyls (e.g., methyl, ethyl, butyl, octyl, etc.); aryl (e.g., benzyl, phenylalkyl, etc.); alkylenes (e.g., methylene, ethylene, octylene, nonylene, tert-butylene, neopentylene, isopropylene, sec-butylene, dodecylene, etc.); alkenylenes (e.g., 1-propenylene, 1-butenylene, 1-pentenylene, 1-hexenylene, 1-heptenylene, 1-octenylene, etc.); cycloalkenylenes (e.g., cyclohexenylene, cyclopentenylene, etc.); hydroxyalkyl (e.g. hydroxymethyl, hydroxyethyl, hydroxyl-n-propyl, hydroxyisopropyl, hydroxyl-n-butyl, hydroxyl-iso-butyl, hydroxyl-tert-butyl, etc.), alkanoylalkylenes (e.g., butanoyl octadecylene, pentanoyl nonadecylene, octanoyl pentadecylene, ethanoyl undecylene, propanoyl hexadecylene, etc.); alkylaminoalkylenes (e.g., methylamino octadecylene, ethylamino pentadecylene, butylamino nonadecylene, etc.); dialkylaminoalkylene (e.g., dimethylamino octadecylene, methylethylamino nonadecylene, etc.); arylaminoalkylenes (e.g., phenylamino octadecylene, p-methylphenylamino nonadecylene, etc.); diarylaminoalkylenes (e.g., diphenylamino pentadecylene, p-nitrophenyl-p'-methylphenylamino octadecylene, etc.); alkylarylaminoalkylenes (e.g., 2-phenyl-4-methylamino pentadecylene, etc.); alkylsulfinylenes, alkylsulfonylenes, alkylthio, arylthio, arylsulfinylenes, and arylsulfonylenes (e.g., butylthio octadecylene, neopentylthio pentadecylene, methylsulfinylnonadecylene, benzylsulfinyl pentadecylene, phenylsulfinyl octadecylene, propylthiooctadecylene, octylthio pentadecylene, nonylsulfonyl nonadecylene, octylsulfonyl hexadecylene, methylthio nonadecylene, isopropylthio octadecylene, phenylsulfonyl pentadecylene, methylsulfonyl nonadecylene, nonylthio pentadecylene, phenylthio octadecylene, ethyltio nonadecylene, benzylthio undecylene, phenethylthio pentadecylene, sec-butylthio octadecylene, naphthylthio undecylene, etc.); alkoxycarbonylalkylenes (e.g., methoxycarbonylene, ethoxycarbonylene, butoxycarbonylene, etc.); cycloalkylenes (e.g., cyclohexylene, cyclopentylene, cyclooctylene, cycloheptylene, etc.); alkoxyalkylenes (e.g., methoxymethylene, ethoxymethylene, butoxymethylene, propoxyethylene, pentoxybutylene, etc.); aryloxyalkylenes and aryloxyarylenes (e.g., phenoxyphenylene, phenoxymethylene, etc.); aryloryalkylenes (e.g., phenoxydecylene, phenoxyoctylene, etc.); arylalkylenes (e.g., benzylene, phenthylene, 8-phenyloctylene, 10-phenyldecylene, etc.); alkylarylenes (e.g., 3-decylphenylene, 4-octylphenylene, 4-nonylphenylene, etc.); and polypropylene glycol and polyethylene glycol substituents (e.g., ethylene, propylene, butylene, phenylene, benzylene, tolylene, p-styrylene, p-phenylmethylene, octylene, dodecylene, octadecylene, methoxyethylene, etc.), as well as combinations thereof. Such tetra-, tri-, and di-ammonium, -sulfonium, -phosphonium, -oxonium; ammonium/sulfonium; ammonium/phosphonium; ammonium/oxonium; phosphonium/oxonium; sulfonium/oxonium; and sulfonium/phosphonium radicals are well known in the art and can be derived from the corresponding amines, phosphines, alcohols or ethers, and sulfides.

Particularly suitable multi-charged spacing/coupling agent compounds are multi-onium ion compounds that include at least two primary, secondary, tertiary or quaternary ammonium, phosphonium, sulfonium, and/or oxonium ions having the following general formula:

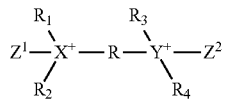

wherein

R is an alkylene, aralkylene or substituted alkylene charged atom spacing moiety; and $Z_1$, $Z_2$, $R_1$, $R_2$, $R_3$, and $R_4$ may be the same or different and selected from the group consisting of hydrogen, alkyl, aralkyl, benzyl, substituted benzyl (e.g., e.g., straight or branched chain alkyl-substituted and halogen-substituted); ethoxylated or propoxylated alkyl; ethoxylated or propoxylated benzyl (e.g., 1-10 moles of ethoxylation or 1-10 moles of propoxylation).

Particularly suitable organic cations may include, for instance, quaternary ammonium compounds, such as dimethyl bis[hydrogenated tallow] ammonium chloride (2M2HT), methyl benzyl bis[hydrogenated tallow] ammonium chloride (MB2HT), methyl tris[hydrogenated tallow alkyl] chloride (M3HT), etc. An example of a suitable nanoclay is Nanomer™ 1.44P, which is a quaternary ammonium modified montmorillonite nanoclay and commercially available from Nanocor, Inc. Other suitable nanoclay additives include those available from Southern Clay Products, such as Cloisite™ 15A, Cloisite™ 30B, Cloisite™ 93A, and Cloisite™ $Na^+$.

The onium ion may be introduced into (sorbed within) the interlayer spaces of the clay material in a number of ways. In one method, for example, the clay material is slurried in water, and the onium ion compound is dissolved therein. If necessary, the onium ion compound can be dissolved first in an organic solvent (e.g., propanol). If desired, the nanoclay may also be intercalated with an oligomer and/or polymer intercalant as is known in the art. For example, an olefin polymer or oligomer (e.g., ethylene polymer) intercalant may be employed. To intercalate an onium ion and an olefin intercalant between adjacent phyllosilicate platelets and optionally separate (exfoliate) the layered material into individual platelets, for example, the clay material may be first contacted with the onium ion and simultaneously or thereafter contacted with the melted oligomer/polymer intercalant to the onium ion-intercalated layered material. This may be accomplished, for instance, by directly compounding the materials in an extruder. Alternatively, the oligomer/polymer can be intercalated by an emulsion process by vigorously mixing with an emulsifier. If desired, a coupling agent (e.g., silane coupling agent) may also be employed to help bond the intercalant with the clay material. For example, the clay material may be initially treated with a coupling agent followed by ion-exchange of onium ions between the clay material, prior to or simultaneously with intercalation of the oligomer(s) or polymer(s). It should be understood that the oligomer or polymer intercalant(s) can also be intercalated between and complexed to the internal platelet faces by other well-known mechanisms, such as by dipole/dipole bonding (direct intercalation of the oligomer or polymer) as described in U.S. Pat. Nos. 5,880,197 and 5,877,248, as well as by acidification with substitution with hydrogen (ion-exchanging the interlayer cations with hydrogen by use of an acid or ion-exchange resin) as described in U.S. Pat. Nos. 5,102,948 and 5,853,886.

C. Compatibilizer

The compatibilizer may be a polyolefin containing an olefin component and a polar component. The olefin component is non-polar and thus generally has an affinity for the ethylene polymer. The olefin component may generally be formed from any linear or branched α-olefin monomer, oligomer, or polymer (including copolymers) derived from an α-olefin monomer. In one particular embodiment, for example, the compatibilizer includes at least one linear or branched α-olefin monomer, such as those having from 2 to 20 carbon atoms and preferably from 2 to 8 carbon atoms. Specific examples include ethylene, propylene, 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin co-monomers are ethylene and propylene.

The polyolefin compatibilizer is also functionalized with a polar component, which can be grafted onto the polymer, incorporated as a monomeric constituent of the polymer (e.g., block or random copolymers), etc. When grafted onto a polymer backbone, particularly suitable polar groups are maleic anhydride, maleic acid, acrylic acid, methacrylic acid, fumaric acid, maleimide, maleic acid hydrazide, a reaction product of maleic anhydride and diamine, methylnadic anhydride, dichloromaleic anhydride, maleic acid amide, etc. Maleic anhydride modified polyolefins are particularly suitable for use in the present invention. Such modified polyolefins are typically formed by grafting maleic anhydride onto a polymeric backbone material. Such maleated polyolefins are available from E. I. du Pont de Nemours and Company under the designation FUSABOND®, such as the P Series (chemically modified polypropylene), E Series (chemically modified polyethylene), C Series (chemically modified ethylene vinyl acetate), A Series (chemically modified ethylene acrylate copolymers or terpolymers), M Series (chemically modified polyethylene), or N Series (chemically modified ethylene-propylene, ethylene-propylene diene monomer ("EPDM") or ethylene-octene). Alternatively, modifier polyolefins are also available from Chemtura Corp. under the designation POLYBOND® (e.g., acrylic acid-modified polypropylene) and Eastman Chemical Company under the designation Eastman G series.

As noted above, the polar component may also be incorporated into the polyolefin compatibilizer as a monomer. For example, a (meth)acrylic monomeric component may be employed in certain embodiments. As used herein, the term "(meth)acrylic" includes acrylic and methacrylic monomers, as well as salts or esters thereof, such as acrylate and methacrylate monomers. Examples of such (meth)acrylic monomers may include methyl acrylate, ethyl acrylate, n-propyl acrylate, i-propyl acrylate, n-butyl acrylate, s-butyl acrylate, i-butyl acrylate, t-butyl acrylate, n-amyl acrylate, i-amyl acrylate, isobornyl acrylate, n-hexyl acrylate, 2-ethylbutyl acrylate, 2-ethylhexyl acrylate, n-octyl acrylate, n-decyl acrylate, methylcyclohexyl acrylate, cyclopentyl acrylate, cyclohexyl acrylate, methyl methacrylate, ethyl methacrylate, 2-hydroxyethyl methacrylate, n-propyl methacrylate, n-butyl methacrylate, i-propyl methacrylate, i-butyl methacrylate, n-amyl methacrylate, n-hexyl methacrylate, i-amyl methacrylate, s-butyl-methacrylate, t-butyl methacrylate, 2-ethylbutyl methacrylate, methylcyclohexyl methacrylate, cinnamyl methacrylate, crotyl methacrylate, cyclohexyl methacrylate, cyclopentyl methacrylate, 2-ethoxyethyl methacrylate, isobornyl methacrylate, etc., as well as combinations thereof. Other types of suitable polar monomers include ester monomers, amide monomers, etc.

D. Other Components

In addition to the components noted above, other additives may also be incorporated into the film of the present invention, such as slip additives, melt stabilizers, processing stabilizers, heat stabilizers, light stabilizers, antioxidants, heat aging stabilizers, whitening agents, bonding agents, fillers, etc. Further, hindered phenols are commonly used as an antioxidant in the production of films. Some suitable hindered phenols include those available from Ciba Specialty Chemicals under the trade name "Irganox®", such as Irganox® 1076, 1010, or E 201. Moreover, bonding agents may also be added to the film to facilitate bonding of the film to additional materials (e.g., nonwoven webs). Examples of such bonding agents include hydrogenated hydrocarbon resins. Other suitable bonding agents are described in U.S. Pat. No. 4,789,699 to Kieffer et al. and U.S. Pat. No. 5,695,868 to McCormack. per II. Film Construction The film of the present invention may be mono- or multi-layered. Multilayer films may be prepared by co-extrusion of the layers, extrusion coating, or by any conventional layering process. Such multilayer films normally contain at least one base layer and at least one skin layer, but may contain any number of layers desired. For example, the multilayer film may be formed from a base layer and one or more skin layers. In one embodiment, for example, it may be desirable to employ two skin layers that sandwich a base layer. Regardless of the particular construction, the skin and/or base layers may be formed from the polymer composition of the present invention. In one embodiment, for example, the base layer is formed from the polymer composition of the present invention and the skin layer(s) are formed from the polymer composition or from an additional polymer material. Likewise, in other possible embodiments, one or more of the skin layers are formed from the polymer composition of the present invention and the base layer is formed from an additional polymer material. When employed, the additional material may include any type of polymer, such as polyolefins (e.g., polyethylene, polypropylene, etc.), polyesters, polyamides, styrenic copolymers, polyurethanes, polyvinyl acetate, polyvinyl alcohol, etc.

When multiple layers are employed, the base layer typically constitutes a substantial portion of the weight of the film, such as from about 50 wt. % to about 99 wt. %, in some embodiments from about 55 wt. % to about 90 wt. %, and in some embodiments, from about 60 wt. % to about 85 wt. % of the film. The skin layer(s) may likewise constitute from about 1 wt. % to about 50 wt. %, in some embodiments from about 10 wt. % to about 45 wt. %, and in some embodiments, from about 15 wt. % to about 40 wt. % of the film. Each skin layer may also have a thickness of from about 0.1 to about 10 micrometers, in some embodiments from about 0.5 to about 5 micrometers, and in some embodiments, from about 1 to about 2.5 micrometers. Likewise, the base layer may have a thickness of from about from about 1 to about 40 micrometers, in some embodiments from about 2 to about 25 micrometers, and in some embodiments, from about 5 to about 20 micrometers. As noted above, the total thickness of the film is typically about 50 micrometers or less, in some embodiments from about 1 to about 40 micrometers, in some embodiments from about 5 to about 35 micrometers, and in some embodiments, from about 10 to about 30 micrometers.

Any of a variety of techniques may generally be employed to form the film of the present invention. In certain embodiments, for example, the components of the film (e.g., ethylene polymer, nanoclay, compatibilizer, etc.) may be individually supplied to a film forming system and blended together as the film is being formed. In such cases, the nanoclay may be in the form of a powder containing particles, such as described above. Alternatively, however, it is may be desirable to pre-blend the ethylene polymer, nanoclay, and/or compatibilizer to form a masterbatch, which is then subsequently supplied to the film forming system. Without intending to be limited by theory, it is believed such a multi-step process can allow the nanoclay to be more uniformly oriented, thereby even further enhancing ductility. When supplied, the nanoclay may itself be in the form of a masterbatch, which may contain nanoclay particles blended with a polymer (e.g., ethylene polymer), or in the form of a powder containing particles.

To form a masterbatch, for example, the components may initially be supplied to twin screw extruder that includes co-rotating screws rotatably mounted and received within a barrel (e.g., cylindrical barrel), which may be heated. The components are moved downstream from a feed end to a discharge end by forces exerted by rotation of the screws. The ratio of the length to outer diameter ("L/D") of the screws may be selected to achieve an optimum balance between throughput and blend uniformity. For example, too large of an L/D value may increase the retention time to such an extent that the nanoclay degrades beyond the desired level. On other hand, too low of an L/D value may not result in the desired degree of blending. Thus, the L/D value is typically from about 25 to about 60, in some embodiments from about 35 to about 55, and in some embodiments from about 40 to about 50. The speed of the screws may also be selected to achieve the desired residence time, shear rate, melt processing temperature, etc. Generally, an increase in product temperature is observed with increasing screw speed due to the additional mechanical energy input into the system. The frictional energy results from the shear exerted by the turning screw on the materials within the extruder and results in the fracturing of large molecules. This results in lowering the apparent viscosity and increasing the melt flow rate of the finished material. For example, the screw speed may range from about 50 to about 400 revolutions per minute ("rpm"), in some embodiments from about 100 to about 300 rpm, and in some embodiments, from about 120 to about 280 rpm. As a result, melt processing may occur at a temperature of from about 100° C. to about 500° C., in some embodiments, from about 150° C. to about 350° C., and in some embodiments, from about 150° C. to about 300° C. Typically, the apparent shear rate during melt processing may range from about 300 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$. The apparent shear rate is equal to $4Q/R^3$, where Q is the volumetric flow rate ("m$^3$/s") of the polymer melt and R is the radius ("m") of the capillary (e.g., extruder die) through which the melted polymer flows. Of course, other variables, such as the residence time during melt processing, which is inversely proportional to throughput rate, may also be controlled to achieve the desired blending.

Once formed, the pre-blended masterbatch may be supplied to a film-forming system. Any known technique may be used to form a film from the compounded material, including blowing, casting, flat die extruding, etc. In one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al. In yet another embodiment, however, the film is formed using a casting technique.

Referring to FIG. 1, for instance, one embodiment of a method for forming a cast film is shown. In this embodiment, the pre-blended masterbatch is supplied to an extruder 80 for melt processing. To help achieve good alignment and orientation of the nanoclay, it is typically desired to use a single screw extruder during film formation. Such single screw extruders are typically divided into three sections along the length of the screw. The first section is a feed section where the solid material is introduced to the screw. The second section is a melting section where a majority of the melting of the solid occurs. Within this section, the screw generally possesses a tapered diameter to enhance melting of the polymer. The third section is the mixing section, which delivers the molten material in a constant amount for extrusion. The L/D ratio for the screw is typically from about 5 to about 50, in some embodiments from about 10 to about 40, and in some embodiments from about 15 to about 35. Such L/D ratios may be readily achieved in a single screw extruder by using mixing section(s) that constitute only a small portion of the length of the screw. The screw speed may likewise range from about 5 to about 150 rpm, in some embodiments from about 10 to about 100 rpm, and in some embodiments, from about 20 to about 80 rpm. As a result, melt processing may occur at a temperature of from about 100° C. to about 500° C., in some embodiments, from about 150° C. to about 350° C., and in some embodiments, from about 150° C. to about 300° C.

Once formed, the extruded material may be immediately chilled and cut into pellet form. In the embodiment of FIG. 1, the extruded material is cast onto a casting roll 90 to form a single-layered precursor film 10a. If a multilayered film is to be produced, the multiple layers are co-extruded together onto the casting roll 90. The casting roll 90 may optionally be provided with embossing elements to impart a pattern to the film. Typically, the casting roll 90 is kept at temperature sufficient to solidify and quench the sheet 10a as it is formed, such as from about 20 to 60° C. If desired, a vacuum box may be positioned adjacent to the casting roll 90 to help keep the precursor film 10a close to the surface of the roll 90. Additionally, air knives or electrostatic pinners may help force the precursor film 10a against the surface of the casting roll 90 as it moves around a spinning roll. An air knife is a device known in the art that focuses a stream of air at a very high flow rate to pin the edges of the film.

Once cast, the film 10a may then be optionally oriented in one or more directions to further improve film uniformity and reduce thickness. In the case of sequential orientation, the "softened" film is drawn by rolls rotating at different speeds of rotation such that the sheet is stretched to the desired draw ratio in the longitudinal direction (machine direction). If desired, the uniaxially oriented film may also be oriented in the cross-machine direction to form a "biaxially oriented" film. For example, the film may be clamped at its lateral edges by chain clips and conveyed into a tenter oven. In the tenter oven, the film may be reheated and drawn in the cross-machine direction to the desired draw ratio by chain clips diverged in their forward travel.

Referring again to FIG. 1, for instance, one method for forming a uniaxially oriented film is shown. As illustrated, the precursor film 10a is directed to a film-orientation unit 100 or machine direction orienter ("MDO"), such as commercially available from Marshall and Willams, Co. of Providence, R.I. The MDO has a plurality of stretching rolls (such as from 5 to 8) which progressively stretch and thin the film in the machine direction, which is the direction of travel of the film through the process as shown in FIG. 1. While the MDO 100 is illustrated with eight rolls, it should be understood that the number of rolls may be higher or lower, depending on the level of stretch that is desired and the degrees of stretching between each roll. The film may be stretched in either single or multiple discrete stretching operations. It should be noted that some of the rolls in an MDO apparatus may not be operating at progressively higher speeds. If desired, some of the rolls of the MDO 100 may act as preheat rolls. If present, these first few rolls heat the film 10a above room temperature. The progressively faster speeds of adjacent rolls in the MDO act to stretch the film 10a. The rate at which the stretch rolls rotate determines the amount of stretch in the film and final film weight. The resulting film 10b may then be wound and stored on a take-up roll 60. While not shown here, various additional potential processing and/or finishing steps known in the art, such as slitting, treating, aperturing, printing graphics, or lamination of the film with other layers (e.g., nonwoven web materials), may be performed without departing from the spirit and scope of the invention.

III. Laminates

Although by no means required, it may be desirable in certain cases to laminate an additional material to the nanocomposite of the film of the present invention, such as fibrous webs (e.g., nonwoven webs), other films, foams, strands, etc. For example, when employed as a backsheet in an absorbent article, the film may be laminated to a nonwoven facing that reduces the coefficient of friction and enhances the cloth-like feel of the laminate surface. Exemplary polymers for use in forming nonwoven web materials may include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. If desired, biodegradable polymers, such as those described above, may also be employed. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. It should be noted that the polymer(s) may also contain other additives, such as processing aids or treatment compositions to impart desired properties to the fibers, residual amounts of solvents, pigments or colorants, and so forth. If desired, the nonwoven facing used to form the laminate may itself have a multi-layer structure. Suitable multi-layered materials may include, for instance, spunbond/meltblown/spunbond (SMS) laminates and spunbond/meltblown (SM) laminates. Various examples of suitable SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al. The basis weight of the nonwoven facing may generally vary, such as from about 5 grams per square meter ("gsm") to 120 gsm, in some embodiments from about 10 gsm to about 70 gsm, and in some embodiments, from about 15 gsm to about 35 gsm. When multiple nonwoven web materials, such materials may have the same or different basis weights.

IV. Absorbent Article

The nanocomposite film of the present invention may be used in a wide variety of absorbent articles. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins, pantiliners, etc.), swim wear, baby wipes, and so forth; medical absorbent articles, such as garments, fenestration materials, underpads, bedpads, bandages, absorbent drapes, and medical wipes; food service wipers; clothing articles; and so forth. Several examples of such absorbent articles are described in U.S. Pat. No. 5,649,916 to DiPalma, et al.; U.S. Pat. No. 6,110,158 to Kielpikowski; U.S. Pat. No. 6,663,611 to Blaney, et al. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Frei burger et al. Materials and processes suitable for forming such absorbent articles are well known to those skilled in the art. Typically, absorbent articles include a generally liquid-impermeable layer (e.g., backsheet), a liquid-permeable layer (e.g., topsheet, surge layer, etc.), and an absorbent core. The nanocomposite film of the present invention, or a laminate thereof, may be used to form any component of the article, such as the backsheet and/or topsheet. In one particular embodiment, the film is employed in the backsheet.

Figure 2:
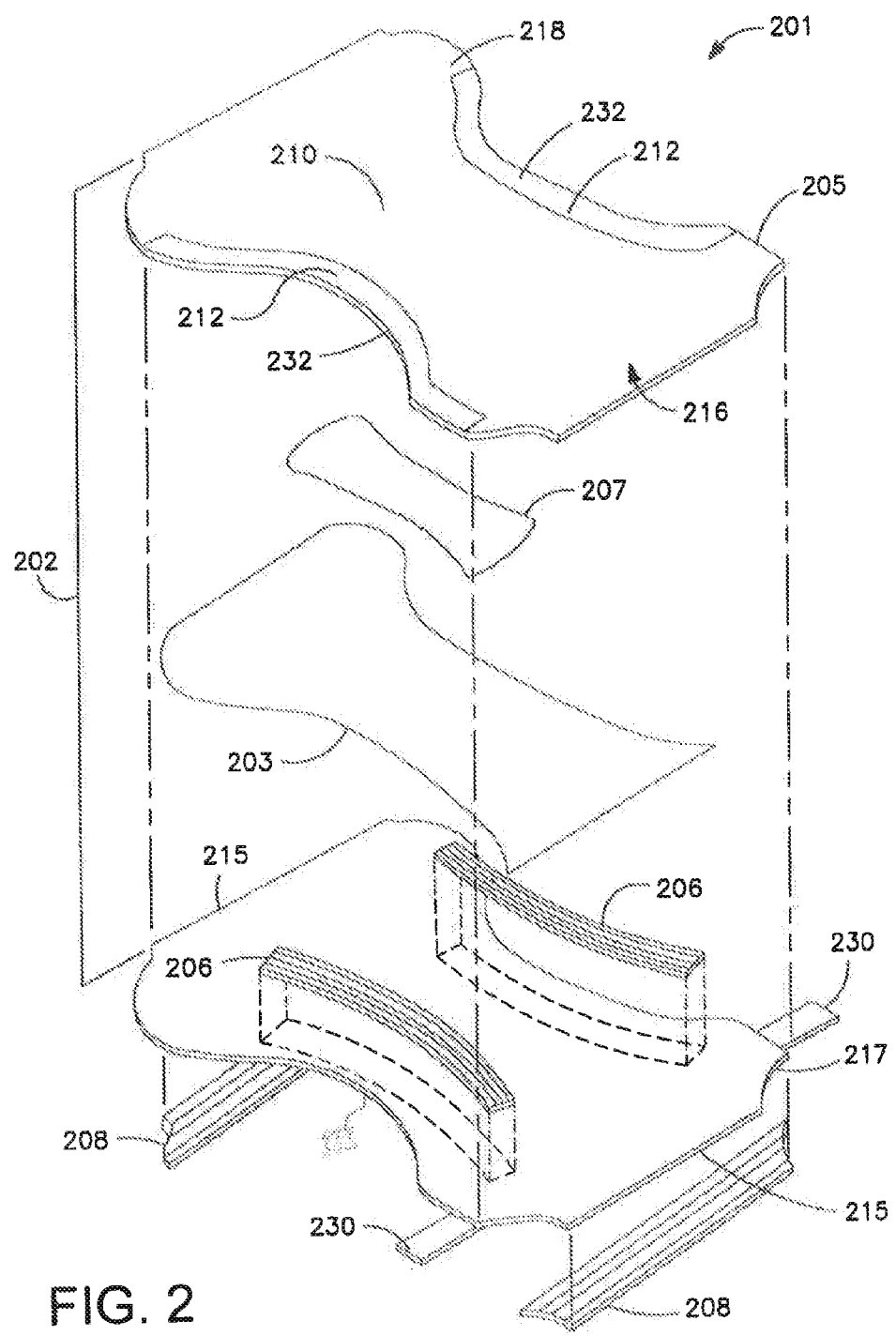
FIG. 2 is a perspective view of one embodiment of the absorbent article of the present invention.

Various embodiments of an absorbent article that may be formed according to the present invention will now be described in more detail. Referring to FIG. 2, for instance, one embodiment of an absorbent article 201 is shown in the form of a diaper. However, as noted above, the invention may be embodied in other types of absorbent articles, such as incontinence articles, sanitary napkins, diaper pants, feminine napkins, children's training pants, and so forth. In the illustrated embodiment, the absorbent article 201 is shown as having an hourglass shape in an unfastened configuration. However, other shapes may of course be utilized, such as a generally rectangular shape, T-shape, or I-shape. As shown, the absorbent article 201 includes a chassis 202 formed by various components, including a backsheet 217, topsheet 205, absorbent core 203, and surge layer 207. It should be understood, however, that other layers may also be used in the present invention. Likewise, one or more of the layers referred to in FIG. 2 may also be eliminated in certain embodiments of the present invention.

As indicated above, the backsheet 217 may be formed from the nanocomposite film of the present invention, which is optionally laminated to a nonwoven facing. In certain cases, the film may be positioned so that it defines a garment-facing surface 333 of the absorbent article 201. The absorbent article 201 also includes a topsheet 205. The topsheet 205 is generally employed to help isolate the wearer's skin from liquids held in the absorbent core 203. For example, the topsheet 205 may define a body-facing surface 218, which is typically compliant, soft feeling, and non-irritating to the wearer's skin. The topsheet may include a nonwoven web (e.g., spunbond web, meltblown web, or bonded carded web). Other exemplary topsheet constructions that contain a nonwoven web are described in U.S. Pat. Nos. 5,192,606; 5,702,377; 5,931,823; 6,060,638; and 6,150,002, as well as U.S. Patent Application Publication Nos. 2004/0102750, 2005/0054255, and 2005/0059941.

As illustrated in FIG. 2, the absorbent article 201 may also include a surge layer 207 that helps to decelerate and diffuse surges or gushes of liquid that may be rapidly introduced into the absorbent core 203. Desirably, the surge layer 207 rapidly accepts and temporarily holds the liquid prior to releasing it into the storage or retention portions of the absorbent core 203. In the illustrated embodiment, for example, the surge layer 207 is interposed between an inwardly facing surface 216 of the topsheet 205 and the absorbent core 203. Alternatively, the surge layer 207 may be located on the outwardly facing surface 218 of the topsheet 205. The surge layer 207 is typically constructed from highly liquid-permeable materials. Suitable materials may include porous woven materials, porous nonwoven materials, and apertured films. Other examples of suitable surge layers are described in U.S. Pat. No. 5,486,166 to Ellis, et al. and U.S. Pat. No. 5,490,846 to Ellis, et al.

Besides the above-mentioned components, the absorbent article 201 may also contain various other components as is known in the art. For example, the absorbent article 201 may also contain a substantially hydrophilic wrapsheet (not illustrated) that helps maintain the integrity of the fibrous structure of the absorbent core 203. The wrapsheet is typically placed about the absorbent core 203 over at least the two major facing surfaces thereof, and composed of an absorbent cellulosic material, such as creped wadding or a high wet-strength tissue. The wrapsheet may be configured to provide a wicking layer that helps to rapidly distribute liquid over the mass of absorbent fibers of the absorbent core 203. The wrapsheet material on one side of the absorbent fibrous mass may be bonded to the wrapsheet located on the opposite side of the fibrous mass to effectively entrap the absorbent core 203. Furthermore, the absorbent article 201 may also include a ventilation layer (not shown) that is positioned between the absorbent core 203 and the backsheet 217. When utilized, the ventilation layer may help insulate the backsheet 217 from the absorbent core 203, thereby reducing dampness in the backsheet 217. Examples of such ventilation layers may include a nonwoven web laminated to a breathable film, such as described in U.S. Pat. No. 6,663,611 to Blaney, et al.

In some embodiments, the absorbent article 201 may also include a pair of ears (not shown) that extend from the side edges 232 of the absorbent article 201 into one of the waist regions. The ears may be integrally formed with a selected diaper component. For example, the ears may be integrally formed with the backsheet 217 or from the material employed to provide the top surface. In alternative configurations, the ears may be provided by members connected and assembled to the backsheet 217, the top surface, between the backsheet 217 and top surface, or in various other configurations.

As representatively illustrated in FIG. 2, the absorbent article 201 may also include a pair of containment flaps 212 that are configured to provide a barrier and to contain the lateral flow of body exudates. The containment flaps 212 may be located along the laterally opposed side edges 232 of the topsheet 205 adjacent the side edges of the absorbent core 203. The containment flaps 212 may extend longitudinally along the entire length of the absorbent core 203, or may only extend partially along the length of the absorbent core 203. When the containment flaps 212 are shorter in length than the absorbent core 203, they may be selectively positioned anywhere along the side edges 232 of absorbent article 201 in a crotch region 210. In one embodiment, the containment flaps 212 extend along the entire length of the absorbent core 203 to better contain the body exudates. Such containment flaps 212 are generally well known to those skilled in the art. For example, suitable constructions and arrangements for the containment flaps 212 are described in U.S. Pat. No. 4,704,116 to Enloe.

The absorbent article 201 may include various elastic or stretchable materials, such as a pair of leg elastic members 206 affixed to the side edges 232 to further prevent leakage of body exudates and to support the absorbent core 203. In addition, a pair of waist elastic members 208 may be affixed to longitudinally opposed waist edges 215 of the absorbent article 201. The leg elastic members 206 and the waist elastic members 208 are generally adapted to closely fit about the legs and waist of the wearer in use to maintain a positive, contacting relationship with the wearer and to effectively reduce or eliminate the leakage of body exudates from the absorbent article 201. The absorbent article 201 may also include one or more fasteners 230. For example, two flexible fasteners 130 are illustrated in FIG. 2 on opposite side edges of waist regions to create a waist opening and a pair of leg openings about the wearer. The shape of the fasteners 230 may generally vary, but may include, for instance, generally rectangular shapes, square shapes, circular shapes, triangular shapes, oval shapes, linear shapes, and so forth. The fasteners may include, for instance, a hook material. In one particular embodiment, each fastener 230 includes a separate piece of hook material affixed to the inside surface of a flexible backing.

The various regions and/or components of the absorbent article 201 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the backsheet 217 and topsheet 205 are assembled to each other and to the absorbent core 203 using an adhesive. Alternatively, the absorbent core 203 may be connected to the backsheet 217 using conventional fasteners, such as buttons, hook and loop type fasteners, adhesive tape fasteners, and so forth. Similarly, other diaper components, such as the leg elastic members 206, waist elastic members 208 and fasteners 230, may also be assembled into the absorbent article 201 using any attachment mechanism.

Although various configurations of a diaper have been described above, it should be understood that other diaper and absorbent article configurations are also included within the scope of the present invention. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth.

The present invention may be better understood with reference to the following examples.

Test Methods

Mechanical Properties:

The strip tensile strength values were determined in substantial accordance with ASTM Standard D638-99. A constant-rate-of-extension type of tensile tester was employed. The tensile testing system was an MTS Synergy 200 tensile frame. The tensile tester was equipped with TESTWORKS 4.08B software from MTS Corporation to support the testing. The load cell was 100 Newtons. The film samples were initially cut into dog-bone shapes with a center width of 3.0 mm before testing. The samples were held between grips having a front and back face measuring 25.4 millimeters×76 millimeters. The grip faces were rubberized, and the longer dimension of the grip was perpendicular to the direction of pull. The grip pressure was pneumatically maintained at a pressure of 40 pounds per square inch. The tensile test was run using a gauge length of 18.0 millimeters and a break sensitivity of 40%. Five samples were tested by applying the test load along the machine-direction and five samples were tested by applying the test load along the cross direction. During the test, samples were stretched at a crosshead speed of about 127 millimeters per minute until breakage occurred. The modulus, peak stress, peak elongation (percent strain at break), and energy per volume at break were measured in the machine direction ("MD") and cross-machine directions ("CD").

Tactile Properties:

Various tactile properties (i.e., softness, smoothness, noise, and silky feeling) of samples were tested using an Adaptable Methodology Panel (AMP) procedure. In this procedure, a small number of testers performed systematic procedures under controlled laboratory conditions. The individual testers were screened for strong sensory ability and received various degrees of training before performing evaluation tasks. Once selected and trained, the testers were asked to assign a scale value to the softness, smoothness, noise, and silky feeling of each sample. For softness, the scale values were either 1, 2, 3, or 4, with 1 being the softest and 4 being the hardest. For smoothness, the scale values were either 1, 1.5, 2, 3, or 4, with 1 being the smoothest and 4 being the roughest. For noise, the scale values were either 1, 2, 2.5, 3, or 4, with 1 being the loudest and 4 being the quietest. For silkiness, the scale values were either 1, 2, 3, or 4, with 1 being the most silky and 4 being the least silky. Average values for obtained for all levels using statistical analysis.

X-Ray Diffraction:

Several film samples were analyzed using X-ray diffraction on a Rigaku D-max Rapid instrument, equipped with a 2-D position sensitive detector. The 2-D patterns were corrected for background, absorption and air scattering and converted to 1-D curves by using azimuthal integration. The WARS detector covers interatomic distances in the range from 2.8 Å to 59 Å (0.28-5.9 nm; 2° is the diffraction angle).

Transmission Electron Microscopy:

Transmission electron microscopy ("TEM") was used to obtain images of film samples in accordance with PSI Method 902 Revision 2. Prior to testing, a portion of each sample was cut away with a razor blade. The samples were then sputter coated in accordance with PSI Method ID 14203 Revision 1 with a layer of gold to increase the chances of finding the sample while performing TEM. The samples were then molded in EpoFix slow cure epoxy. The samples were cross-sectionally cryomicrotomed in accordance with PSI Method ID 904 Revision 3 to produce sections of about 70 nm thickness. The samples were cut parallel to the extruded direction of each sample in order to provide images perpendicular to the extruded direction of the samples.

Noise Level:

Noise levels of film and absorbent article samples may be tested in an apparatus comprised of a test chamber, a control chamber, and a sound level meter. The purpose of the apparatus is to manipulate an article in a controlled noise environment, and to accurately quantify the noise produced by the movement of the sample. In general terms, a sample is physically deformed within the test apparatus to generate a noise level. As used herein, the "noise level" refers to the equivalent continuous noise level (referred to as "$L_{EQ}$" or "$L_{AT}$"), which is the time average sound level (expressed in units of dB) as determined according to the following equation:

$$L_{eq} = 10\log\left[\frac{1}{t_2 - t_1}\int_{t_1}^{t_2}\frac{p_A^2}{p_0^2}dt\right]$$

$p_0$ is a reference pressure level (typically 20 µPa);
$p_A$ is the acquired sound pressure;
t is time;
$t_1$ is the start time for measurement; and
$t_2$ is the end time for measurement.

This value is also described in IEC 61672-1 (2013).

Figure 12:
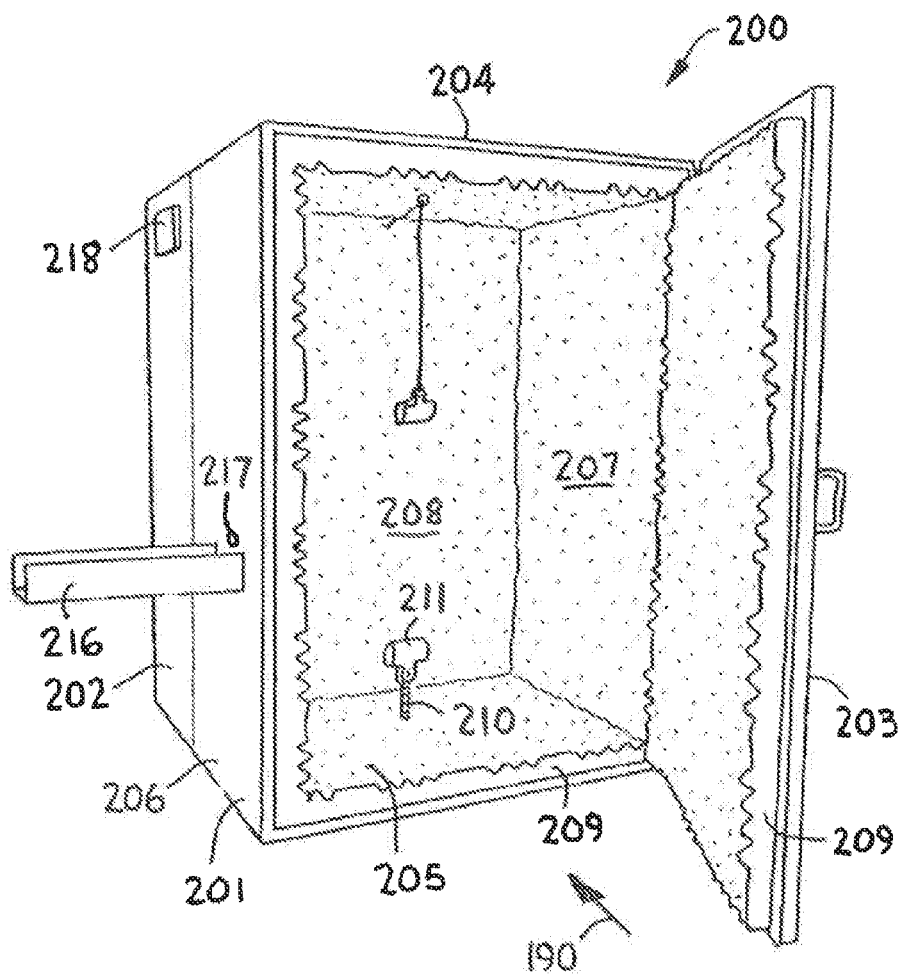
FIG. 12 is a perspective view of a testing apparatus that may be used to evaluate noise levels, with the apparatus door open.
Figure 13:
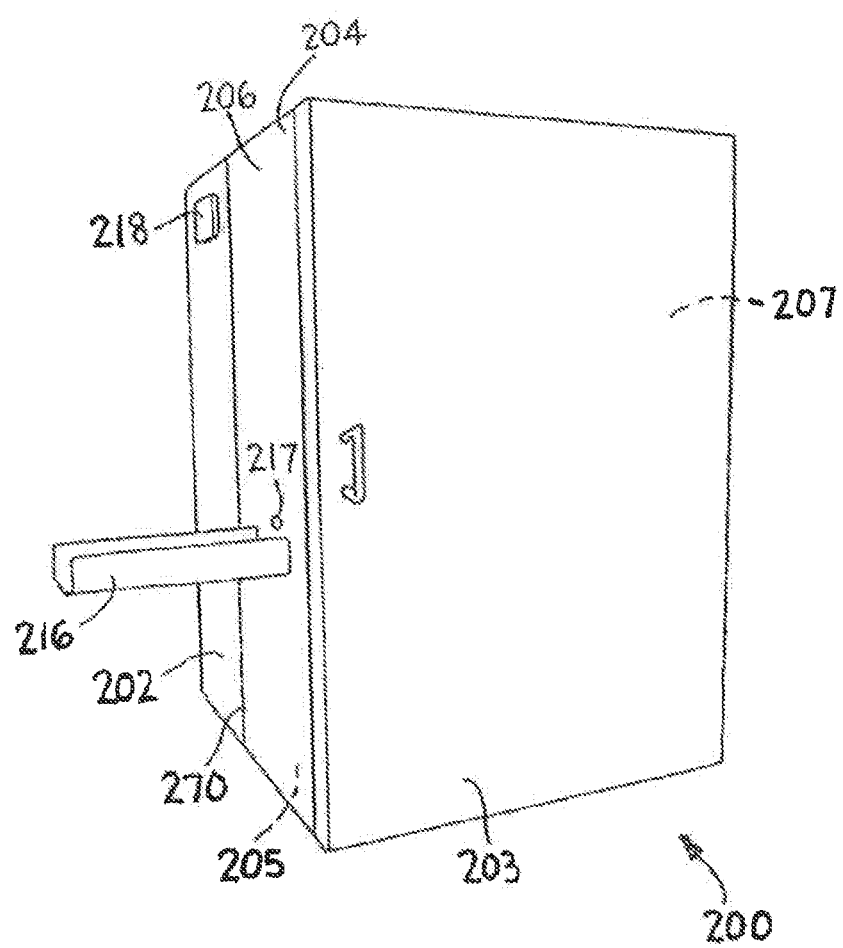
FIG. 13 is a perspective view of the testing apparatus of FIG. 12, with the apparatus door closed.
Figure 14:
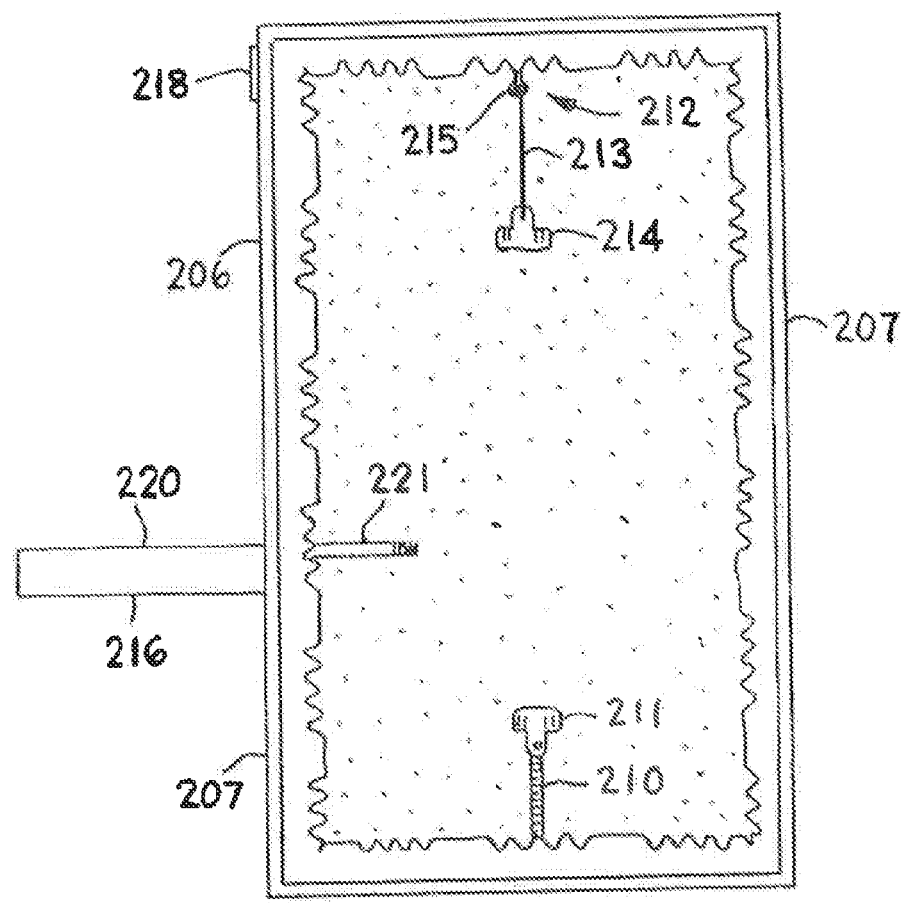
FIG. 14 is a plan view of the apparatus of FIG. 12 taken along arrow 190.

The testing apparatus is illustrated in FIGS. 12-14. The testing apparatus 200 includes a test chamber 201 and a control chamber 202. The test chamber 201 includes a door 203, a top wall 204, a bottom wall 205, two side walls 206 and 207, and a rear wall 208. The door and each wall are constructed of 0.25-inch (0.635 cm) thick 6061 grade anodized aluminum. The door 203 and rear wall 208 are each 36 inches (91.4 cm) in height and 24 inches (61.0 cm) in width. The test chamber side walls 206 and 207 are each 36 inches (91.4 cm) high and 18 inches (45.7 cm) wide. The test chamber top and bottom panels are each 24 inches wide (61.0 cm) and 18 inches (45.7 cm) long. The interior surface of the door 203 and each wall 204-208 has applied thereto two-inch thick polyurethane sound-dampening foam 209, available from Illbruck Inc. under the brand name SONEX and stock number SOC-2. As shown, a sound level meter support 216 extends perpendicularly outward from side wall 206 just below a microphone orifice 217. The microphone orifice 217 is positioned 14.5 centimeters above the floor of the bottom wall 205, and is further centered between the door 203 and the rear wall 208. The sound level meter support 216 is constructed of aluminum and is bolted (not shown) to side wall 206. The control chamber 202 includes a front wall 230, two side walls 231 and 232, a top wall 233, and a bottom wall 234. Each wall is constructed of 0.125-inch (0.3175 cm) thick 6061 grade anodized aluminum. The front wall 230 is 36 inches (91.4 cm) high and 24 inches (61.0 cm) wide. The control chamber side walls 231 and 232 are each 36 inches high (91.4 cm) and 12 inches (30.5 cm) wide. The control chamber top and bottom walls 233 and 234 are each 24 inches (61.0 cm) wide and 12 inches (30.5 cm) long. The control chamber 202 is bolted (not shown) to the outer surface of rear wall 208 along seam 270 (FIG. 13). The outer surface of the rear wall 208, and the front wall 230, two side walls 231 and 232, top wall 233, and bottom wall 234 of the control chamber 202 are each coated with 0.600-inch (1.524 cm) thick sound insulating material, part number NYC-600BE, available from Small Parts, Inc. The testing apparatus 200 further includes a sound level meter 220 (FIG. 14), such as a model 1900, equipped with a model OB-100 octave filter set, both available from Quest Technologies, a company having offices in Oconomowoc, Wis. The sound level meter is supported by a model QC-20 calibrator and QuestSuite master module software, each also available from Quest Technologies. The software is installed on a personal computer (not shown). During operation of the testing apparatus, the sound level meter 220 rests in the sound level meter support 216. The sound level meter includes a microphone 221 extending 4.75 inches (12 centimeters) therefrom.

Although by no means required, the apparatus may also contain features for automatically deforming a sample during a test. For example, the apparatus may contain a lower slide bracket 210, a six-inch (15.24 cm) high Series A1500 Model available from Velmex, Inc., which extends from the bottom wall 205 into the test chamber 201, and a lower clamp 211 that is affixed to the lower slide bracket 210. An eyelet 212 (FIG. 14) may optionally extend from the top wall 204 into the test chamber 201, and an optional lanyard 213 extends through the eyelet 212. One end of the lanyard 213 extends into the test chamber 201, and has an upper clamp 214 affixed thereto. The other end of the lanyard 213 extends into the control chamber 202 through a lanyard orifice 215, which is ⅝ inch (16 mm) in diameter. The lanyard may be a premium-braid, 80-lb test Spiderwire®, part number SB80G-300, manufactured by Johnson Worldwide Associates (JWA), Inc.

Prior to testing a specimen using the testing apparatus 200, the following steps are followed:

1. Calibrate the sound level meter 220 following the instructions in the manufacturer's manual.
2. Insert the full length of the microphone 221 into the testing chamber 201 (it should extend past the wall and sound dampening material approximately 2.5 inches (6.35 cm)), positioned at a 90-degree angle to side wall 206. Allow the sound level meter 220 to rest in the sound level meter support 216.
3. Activate the sound level meter per the manufacturer's instruction manual. This will collect the ambient noise inside the cavity of the test chamber 200.
4. Set the octave filter to 2,000 or 4,000 Hz and take a reading for each test conducted by activating the sound level meter until the testing has been completed.

Having calibrated the testing apparatus 200 and having identified the ambient noise, five (5) specimens of a sample (film or absorbent article) may then be physically deformed approximately 15 to 20 centimeters from the microphone within the test apparatus.

The film samples in the Examples below were manually deformed as follows:

1. Open the dominant hand with the palm facing upward;
2. Place the film sample in the palm of the dominant hand;
3. Compress the test specimen by making a gentle fist;
4. Quickly open the hand and release the test specimen; and
5. Repeat this four (4) more times to equate to five (5) film "crumples."

Figure 15:
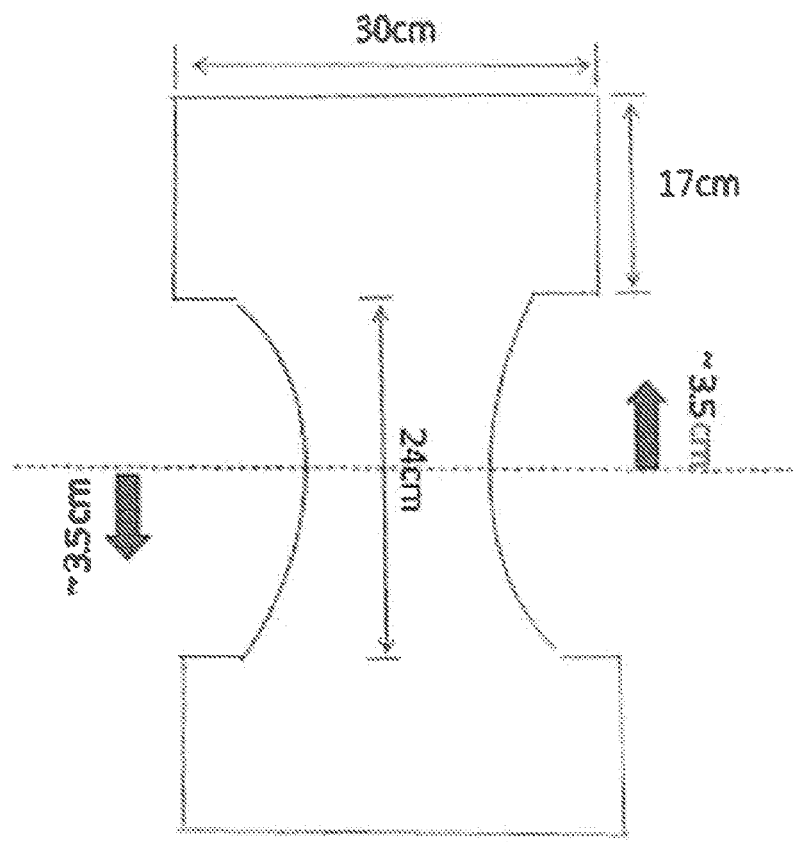
FIG. 15 is a graphical depiction of the absorbent article of Controls 3-4 and Examples 26-27, which shows the manner in which it was laterally stretched to determine the noise level.

The absorbent article samples in the Examples below were also manually deformed using a lateral stretching technique, such as shown by the directional arrows of FIG. 15.

Regardless of the manner of physical deformation, the tests ranged between 1 to 2 seconds in duration. All tests involved starting the sound level meter, completing the respective product manipulation, and then stopping the sound level meter. The chamber door was allowed to remain open during testing to accommodate the arms and hands of the tester, as well as the motions of the product manipulation protocols. The ambient noise outside of the apparatus was quiet and was the same during calibration (including measuring the ambient noise level) and testing of the sample.

Control 1

A film was formed from Dowlex™ EG 2244G using a HAAKE Rheomex® 252p single screw extruder. Dowlex™ EG2244G is a linear low density polyethylene having a melt flow index of 1.0 g/10 minutes at 190° C. (Dow Chemical). The screw had a diameter of 19.05 mm and an L/D of 25 (L is the screw length). A chill roll was used to cool and flatten the polymer as it exited the cast film die. The screw speed was maintained at 60 rpm for a target thickness of 27.94 micrometers. The four controlled temperature zones from the first heating zone to the die adaptor were set at 190° C., 190° C., 190° C., and 190° C., respectively. The residence time was about 1 minute during extrusion.

Control 2

A film was formed as described in Control 1, except that the target thickness was 12.7 micrometers and the screw speed was about 30 rpm.

Example 1

Film layers were formed from blends containing various percentages of LLDPE (Dowlex™ EG 2244G) and a nanoclay masterbatch (Nanocor™ available from Nanocor, Inc.), as reflected below in Table 1. The nanoclay masterbatch contained 50 wt. % Nanomer™ nanoclay (quaternary ammonium surface-modified montmorillonite) and 30 wt. % low density polyethylene and 20% maleic anhydride grafted polyethylene. The blends were formed using a Werner & Pfleiderer (W&P) ZSK-30 co-rotating, twin screw extruder. The extruder had 14 processing barrels, with 13 heated barrels. Three barrels are open barrels. The outer diameters of the screws were 30 mm and the inner screw diameters were 21.3 mm. The lengths of the screws were 1328 mm and the total processing section length was 1338 mm. The zones had a processing temperature of 170° C., 180° C., 190° C., 190° C., 190° C., 190° C., and 180° C., respectively. The melt temperature was about 202° C. and the pressure was about 60-80 psi. The compounding speed in the twin screw extruder was set as 250 rpm.

Once formed, the blends were formed into a film layer having a target thickness of 28 micrometers using a HAAKE single screw extruder as described in Control 1. The resulting samples were then conditioned overnight at 23±2° C. and 50±5% RH and subjected to mechanical testing as described above. The results are set forth below in Table 1.

TABLE 1

Mechanical Properties of the Films of Example 1

|  | LLDPE (wt. %) | Nanoclay Masterbatch (wt. %) | Avg. Peak Stress (MPa) | | Avg. Peak Elongation (%) | | Avg. Modulus (MPa) | | Avg. Energy Per Volume at Break (J/cm$^3$) | |
| --- | --- | --- | --- | --- | --- | --- | --- | --- | --- | --- |
|  |  |  | MD | CD | MD | CD | MD | CD | MD | CD |
| Control 1 | 100 | — | 36 | 26 | 544 | 759 | 61 | 55 | 76 | 87 |
|  | 96 | 4 | 41 | 31 | 625 | 859 | 116 | 115 | 99 | 111 |
| Example 1 | 90 | 10 | 40 | 34 | 591 | 903 | 128 | 143 | 105 | 140 |
|  | 84 | 16 | 40 | 33 | 581 | 873 | 165 | 154 | 112 | 138 |

As indicated, the mechanical properties (e.g., peak elongation) generally improved with the incorporation of nanoclay. In the machine direction (MD), a higher amount of nanoclay led to a slightly lower strain-at-break and higher elastic modulus due to the rigid nature of nanoclay, but the elongation in MC and CD are still higher than the control film without nanoclay, although the peak stress was approximately the same.

Figure 3:
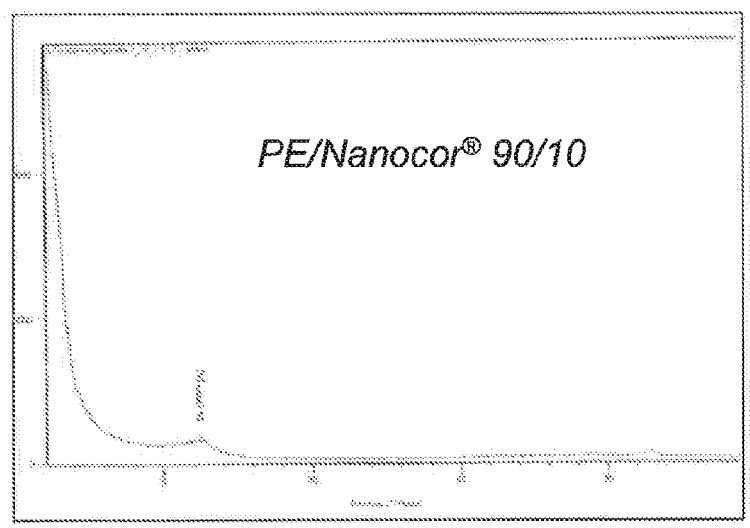
FIG. 3 is an X-ray diffraction graph for Example 1.
Figure 4:
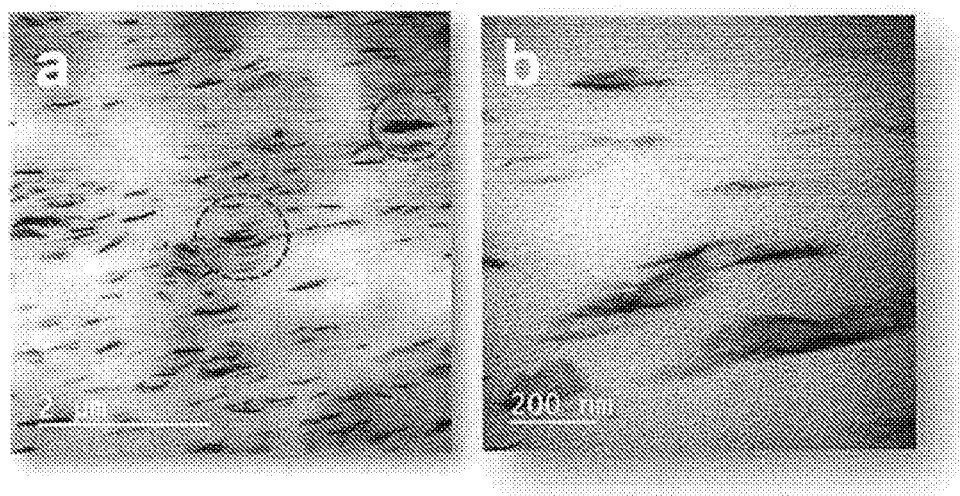
FIG. 4 are transmission electron microphotographs of Example 1 in which FIG. 4($a$) is at a lower magnification (depicted scale of 2 μm) and FIG. 4($b$) is at a higher magnification (depicted scale of 200 nm)

The film of Example 1 (10 wt. % nanoclay masterbatch) was also analyzed using X-ray diffraction and transmission electron microscopy. The results are shown in FIGS. 3-4. As depicted in FIG. 3, only a small peak was observed at an angle of about 7°, which indicates that only a small portion of the nanoclay remained unexfoliated or undispersed. This is further evidenced by the transmission electron microphotographs shown in FIG. 4. Namely, FIG. 4(a) shows that the nanoclay was well dispersed in the film and FIG. 4(b) shows that the nanoclay was exfoliated into single platelets (FIG. 4(b)) and dispersed in orientation. Minor nanoclay clusters were also seen in the film as represented by the circles.

Figure 5:
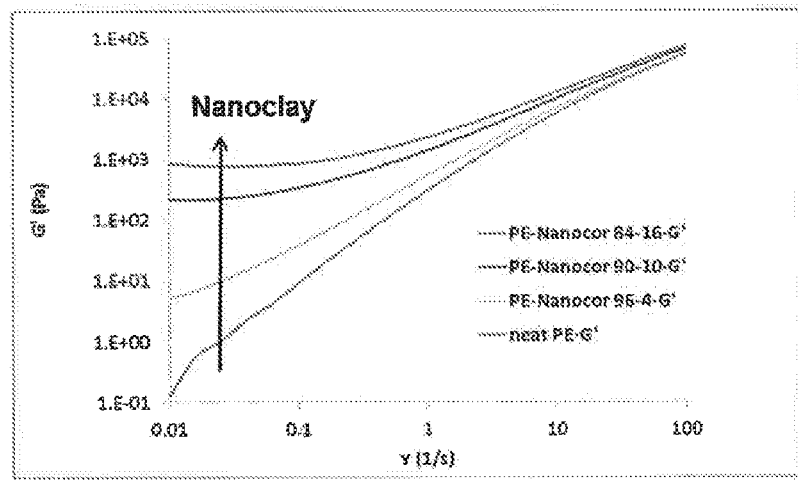
FIG. 5 is a graph that depicts logarithmic storage modulus (G') vs. logarithmic frequency ($\gamma$) for the samples of Example 1.
Figure 6:
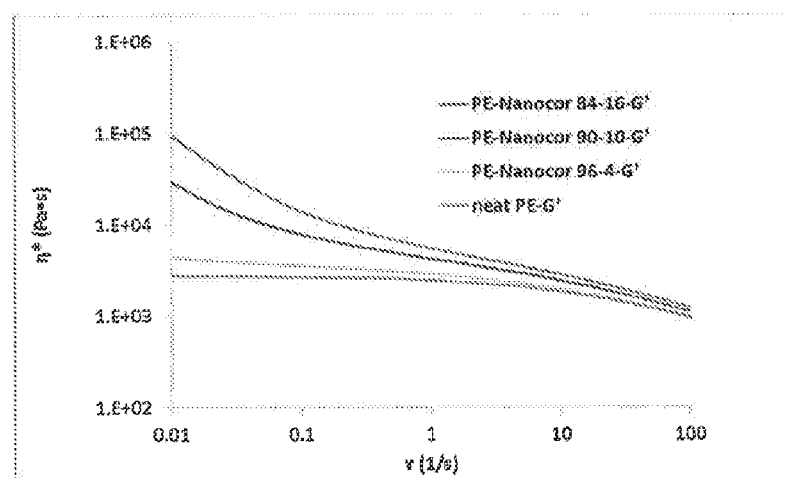
FIG. 6 is a graph that depicts complex viscosity $\eta^*$ vs. logarithmic frequency ($\gamma$) for the samples of Example 1.
Figure 7:
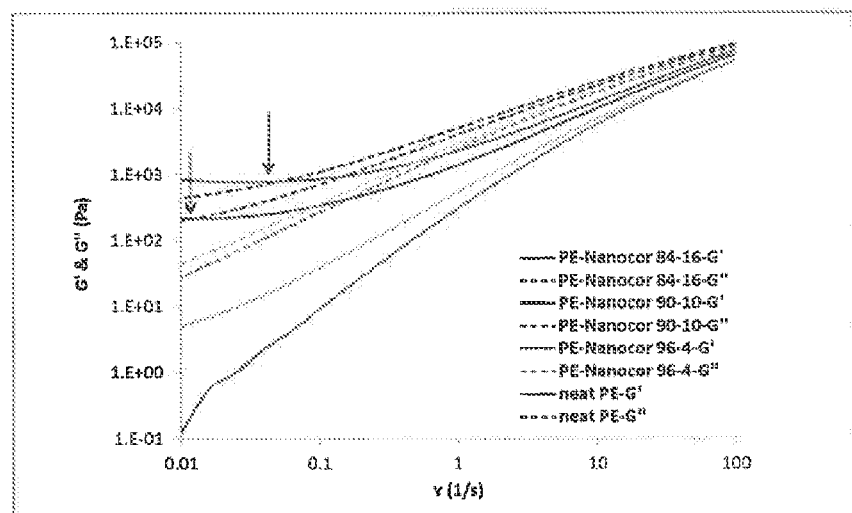
FIG. 7 is a graph that depicts log G' (storage modulus) and log G" (loss modulus) vs. logarithmic frequency ($\gamma$) for the samples of Example 1.
Figure 8:
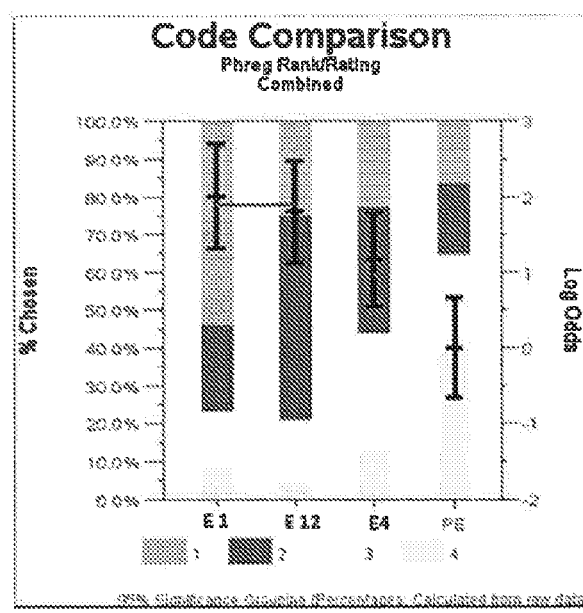
FIG. 8 is a graphical comparison of the softness of Control 1, Example 1, Example 2, and Example 12 as determined using an adaptable methodology sensory panel.
Figure 9:
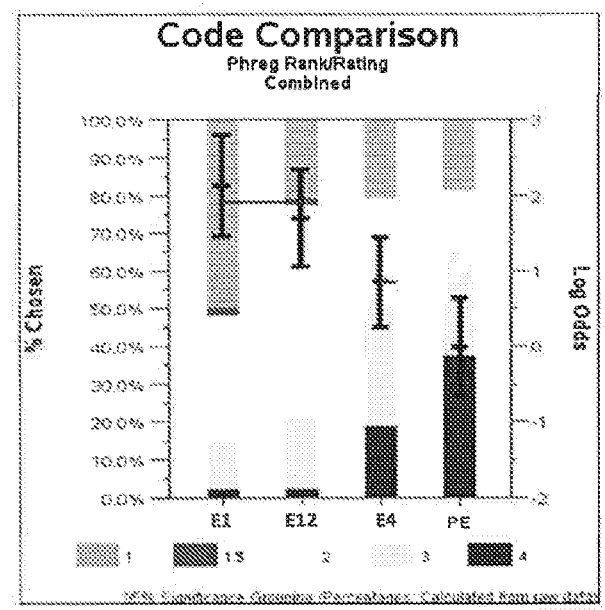
FIG. 9 is a graphical comparison of the smoothness of Control 1, Example 1, Example 2, and Example 12 as determined using an adaptable methodology sensory panel.
Figure 10:
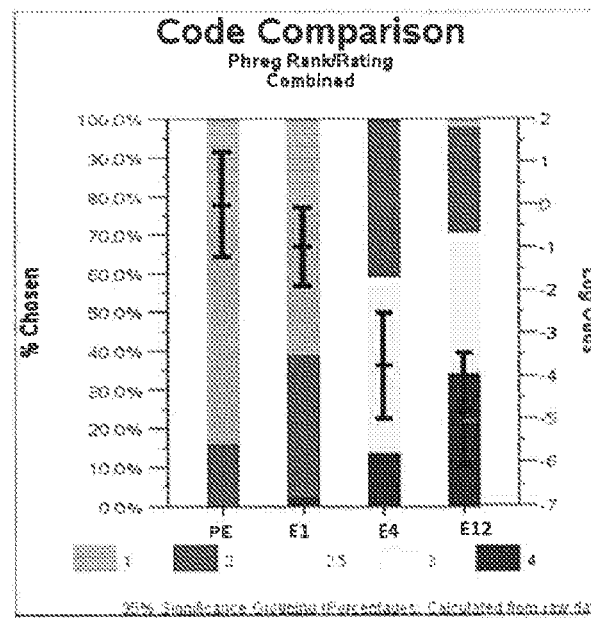
FIG. 10 is a graphical comparison of the noise of Control 1, Example 1, Example 2, and Example 12 as determined using an adaptable methodology sensory panel.
Figure 11:
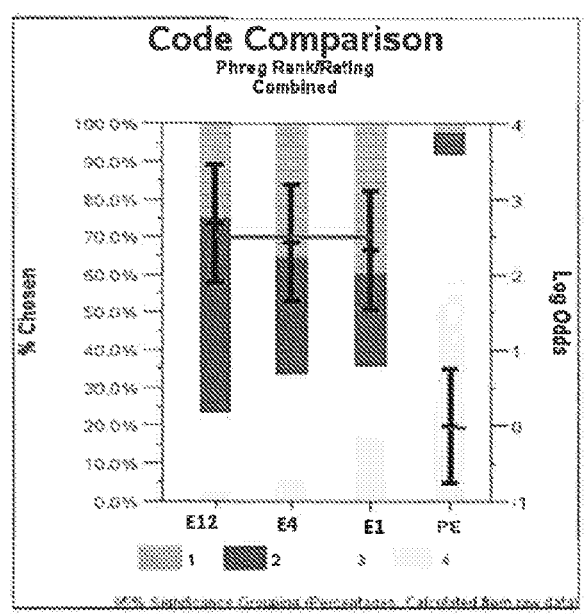
FIG. 11 is a graphical comparison of the silkiness of Control 1, Example 1, Example 2, and Example 12 as determined using an adaptable methodology sensory panel.

Dynamic rheology testing was also performed on Control 1 and the samples containing 4 wt. %, 10 wt. %, and 16 wt. % of the nanoclay masterbatch. The results are shown in FIGS. 5-7. In the terminal (low frequency) zone, the neat LLDPE melt demonstrated a typical liquid like behavior—logarithmic storage modulus (G') vs. logarithmic frequency (γ) showed a smooth linear relationship (lower curve in FIG. 5). The remaining films containing the nanoclay masterbatch not only exhibited much higher G' and complex viscosity (η*) values than neat LLDPE, but also demonstrated drastically different terminal behaviors. Irrespective of frequency, G' increased monotonically with increasing nanoclay content in the blends (FIG. 5). The viscoelastic response of the blends was mainly altered at low frequencies, where G' exhibited weak frequency dependences (FIG. 5). The small slope of log(G') vs. log(γ) in the films containing 10 wt. % nanoclay masterbatch (labeled as "90/10") and 16 wt. % masterbatch (labeled as "84/16") indicates a significant pseudo-solid-like behavior of the melt. This result suggests that an interconnected network structure of anisometric filler—a characteristic solid or gel-like structure had formed in the system. From FIG. 5, it can be seen that the reduction of the slope of log(G') vs. log(γ) with respect to the neat polymer became phenomenal at 10% nanoclay masterbatch ("90/10"), suggesting the critical content of nanoclay for the percolation threshold.

On the other hand, in the terminal zone the plots of log(η*) vs. log(γ) changed from a Newtonian (primary) plateau (lower curve in FIG. 6) for the neat LLDPE to a clear shear-thinning behavior for the blends, providing more evidence of elastic behavior due to the solid network structure of nanoclay. Further evidence of the formation of a pseudo-solid-like network of percolated threads is also noted in FIG. 7, where variations of storage modulus (G') and loss modulus (G") of the blend films vs. γ are compared. The nanofilms with a low nanoclay content (e.g., 4 wt. % nanoclay, "96/4") displayed a lower G' than G" over the whole frequency range. However, with the buildup of network structure, in the terminal zone G' exceeded G" due to the pseudo-solid like behavior. At higher frequencies, crossover of G' and G" was noted, which was probably due to the destruction of the network structure at high shear rates. Expectedly, the crossover of G' and G" was observed for all those nanofilms with nanoclay contents equal to or higher than 10%. It is worth mentioning that the crossover point shifted to higher frequency with more nanoclay in the blends, as can been seen by the blue arrows in FIG. 7.

Example 2

Film layers were formed as described in Example 1, except that the target thickness was 12.7 micrometers. The results are set forth below in Table 2.

TABLE 2

Mechanical Properties of the Films of Example 2

|  | LLDPE (wt. %) | Nanoclay Masterbatch (wt. %) | Avg. Peak Stress (MPa) | | Avg. Peak Elongation (%) | | Avg. Modulus (MPa) | | Avg. Energy Per Volume at Break (J/cm$^3$) | |
| --- | --- | --- | --- | --- | --- | --- | --- | --- | --- | --- |
|  |  |  | MD | CD | MD | CD | MD | CD | MD | CD |
| Control 2 | 100 | — | 35 | 26 | 391 | 818 | 103 | 39 | 53 | 75 |
| Example 2 | 96 | 4 | 37 | 29 | 452 | 809 | 137 | 129 | 68 | 91 |
|  | 90 | 10 | 44 | 28 | 404 | 852 | 185 | 133 | 80 | 97 |
|  | 84 | 16 | 41 | 24 | 435 | 810 | 146 | 144 | 82 | 84 |
|  | 78 | 22 | 61 | 25 | 351 | 765 | 245 | 200 | 119 | 106 |
|  | 72 | 28 | 51 | 22 | 294 | 631 | 291 | 233 | 88 | 80 |
|  | 66 | 34 | 52 | 19 | 254 | 540 | 396 | 250 | 88 | 67 |

As indicated, the mechanical properties (e.g., peak elongation) generally improved with the incorporation of nanoclay. In the machine direction (MD), a higher amount of nanoclay led to a slightly lower strain-at-break and higher elastic modulus due to the rigid nature of nanoclay, although the peak stress was approximately the same.

Example 3

Film layers were formed from a blend containing 96 wt. % Dowlex™ EG 2244G and 4 wt. % of a Nanocor™ masterbatch. The blend was formed using a Werner & Pfleiderer (W&P) ZSK-30 co-rotating, twin screw extruder as described in Example 1, except that the screw speed was 150 rpm. The blend was formed into film having a target thickness of 27.94 micrometers and 12.7 micrometers using a HAAKE single screw extruder as described in Control 1 and 2. The resulting samples were then conditioned overnight at 23±2° 0 and 50±5% RH and subjected to mechanical testing as described above. The results are set forth below in Table 3.

TABLE 3

Mechanical Properties of the Films of Example 3

| | Thickness (μm) | LLDPE (wt. %) | Nanoclay Masterbatch (wt. %) | Avg. Peak Stress (MPa) | | Avg. Peak Elongation (%) | | Avg. Modulus (MPa) | | Avg. Energy Per Volume at Break (J/cm³) | |
|---|---|---|---|---|---|---|---|---|---|---|---|
| | | | | MD | CD | MD | CD | MD | CD | MD | CD |
| Control 1 | 27.94 | 100 | — | 36 | 26 | 544 | 759 | 61 | 55 | 76 | 87 |
| Control 2 | 12.70 | 100 | — | 35 | 26 | 391 | 818 | 103 | 39 | 53 | 75 |
| Example 3 | 27.94 | 96 | 4 | 41 | 33 | 641 | 912 | 121 | 120 | 98 | 127 |
| | 12.70 | 96 | 4 | 41 | 29 | 473 | 815 | 154 | 122 | 72 | 99 |

Example 4

A film layer was formed from a blend containing 93 wt. % Dowlex™ EG 2244G, 5 wt. % Nanomer™ 1.44P (quaternary ammonium surface-modified montmorillonite), and 2 wt. % of Fusabond® MB-528D, which is a graft copolymer of polyethylene and maleic anhydride available from DuPont. The film layer was formed on a HAAKE single-screw extruder. The screw had a diameter of 19.05 mm and an L/D of 25 (L is the screw length). A chill roll was used to cool and flatten the polymer as it exited the cast film die. The screw speed was maintained at 20 rpm. The four controlled temperature zones from the first heating zone to the die adaptor were set at 180° C., 180° C., 180° C., and 190° C., respectively. The die pressure was 19 bar and the torque was 7 N-m.

Examples 5-11

Various films were formed from the film of Example 4 and one or more additional film layers. The additional film layers were formed on a HAAKE single-screw extruder using the materials and conditions set forth below:

| Example | 1st Outer Layer | Core Layer | 2nd Outer Layer |
|---|---|---|---|
| 5 | Film A | Film of Example 8 | Film A |
| 6 | Film C | Film of Example 8 | Film C |
| 7 | Film A | Film of Example 8 | Film C |
| 8 | Film A | — | Film of Example 4 |
| 9 | Film of Example 4 | Film A | Film of Example 4 |
| 10 | Film D | Film of Example 8 | Film D |
| 11 | Film E | Film of Example 8 | Film E |

| Film | Material | Speed (RPM) | Zone 1 (° C.) | Zone 2 (° C.) | Zone 3 (° C.) | Die Temp (° C.) | Die pressure (Bar) | Torque (N·m) |
|---|---|---|---|---|---|---|---|---|
| A | 100% Dowlex™ EG 2244G | 20 | 180 | 180 | 180 | 190 | 27 | 17 |
| B | 100% M3661 | 20 | 180 | 180 | 180 | 190 | 15 | 7 |
| C | 100% DPDA-3220 N 7 | 20 | 180 | 180 | 180 | 190 | 24 | 12 |
| D | 100% Escorene™ Ultra LD 706.15 | 50 | 180 | 180 | 180 | 190 | 20 | 7 |
| E | 100% Vistamaxx™ 3980 | 10 | 180 | 180 | 180 | 190 | 11 | 5 |

M3661 is a polypropylene available from Total Petrochemicals USA (Houston, Tex.). DPDA-3220 N 7 is a high density polyethylene with a melt flow of 2.0 g/10 minutes at 190° C., and available from Dow Chemical Company (Midland, Mich.). Escorene™ Ultra LD 706.15 is ethylene vinyl acetate ("EVA") available from ExxonMobil (Houston, Tex.). Vistamaxx™ 3980, a propylene-based elastomer available from ExxonMobil (Houston, Tex.).

The films were formed using a 15-ton hydraulic Carver press. The press had two platens set at 205° F. The dwell time was 2 minutes under a 13,000-lb force. The films had the following configurations:

Once formed, the films were conditioned at 75° F./50% relative humidity. After conditioning 24 hours, the films were removed from conditioning and subjected to mechanical testing as described above. The results are set forth below in Table 4.

TABLE 4

Mechanical Properties of the Films of Examples 5-11

| Example | | Thickness (mil) | Peak Stress (MPa) | Peak Elongation (%) | Modulus (MPa) | Energy per Volume at Break (J/cm³) |
|---|---|---|---|---|---|---|
| 5 | MD | 1.8 | 41 | 408 | 165 | 79 |
| | CD | 2.1 | 14 | 428 | 332 | 46 |
| 6 | MD | 1.9 | 20 | 327 | 295 | 57 |
| | CD | 1.3 | 5 | 65.6 | 46 | 3 |
| 7 | MD | 1.9 | 21 | 253 | 226 | 33 |
| | CD | 1.9 | 9 | 445 | 272 | 36 |
| 8 | MD | 1.3 | 6 | 198 | 98 | 11 |
| | CD | 1.4 | 5 | 66 | 46 | 3.0 |

TABLE 4-continued

Mechanical Properties of the Films of Examples 5-11

| Example | | Thickness (mil) | Peak Stress (MPa) | Peak Elongation (%) | Modulus (MPa) | Energy per Volume at Break (J/cm³) |
|---|---|---|---|---|---|---|
| 9 | MD | 2.0 | 9 | 412 | 159 | 28 |
|   | CD | 2.1 | 6 | 122 | 149 | 14 |
| 10 | MD | 4.7 | 9 | 450 | 57 | 33 |
|   | CD | 5.1 | 8 | 429 | 61 | 28 |
| 11 | MD | 1.3 | 12 | 473 | 94 | 39 |
|   | CD | 1.2 | 13 | 494 | 859 | 32 |

Example 12

A film layer was formed from a blend containing 90 wt. % Dowlex™ EG 2244G and 10 wt. % of a nanoclay masterbatch. The nanoclay masterbatch contained a blend of 50 wt. % Clayton™ HY, 30 wt. % Dowlex EG2244G, and 20 wt. % of Fusabond® MB-528D. Clayton™ HY is an organoclay powder treated with quaternary ammonium solution and is available from BYK Additives, Inc. (Gonzales Tex.). The nanoclay masterbatch was formed on a Thermo Prism USALab16 co-rotating twin screw microextruder (Thermo Electron Corporation; Stone, England) having an L/D ratio of 40:1. The LLDPE and Fusabond® components were fed through the pellet feeders and the Clayton™ HY organoclay powder was fed using a powder feeder. The processing temperatures along the 10-zone extruder were 170° C., 180° C., 185° C., 180° C., 185° C., 185° C., 185° C., 185° C., 185° C., and 180° C., respectively. The melt pressure was about 30 psi and the compounding speed was 100 rpm. The LLDPE and nanoclay masterbatch were thereafter compounded on a ZSK-30 twin screw extruder as described in Example 1. A film layer was thereafter produced from the resulting blend using a HAAKE single-screw extruder as described in Control 1.

The films of the present invention may also possess enhanced tactile properties, such as a high degree of softness, smoothness, and silkiness, as well as reduced level of noise. To this end, the tactile properties of Example 12, as well as Control 1, Example 1 (10 wt. % nanoclay masterbatch), and Example 2 (10 wt. % nanoclay masterbatch) were each tested in the manner described above. The results are shown in FIGS. 8-11. As shown, all of the nanoclay film samples (Example 1, Example 2, and Example 12) were softer, smoother, and quieter than the neat polyethylene film (Control 1). Likewise, Example 12 (contained Clayton® HY nanoclay) was softer, smoother, and quieter than Example 2 (contained Nanocor® nanoclay).

Example 13

A film layer was formed as described in Example 12, except that the nanoclay used is Cloisite™ 15A, instead of Clayton™ HY.

Example 14

A film layer was formed as described in Example 12, except that the nanoclay used is Cloisite™ 30B, instead of Clayton™ HY.

Example 15

A film layer was formed as described in Example 12, except that the nanoclay used is Cloisite™ 93A, instead of Clayton™ HY.

Example 16

A film layer was formed as described in Example 12, except that the nanoclay used is Cloisite™ Na⁺, instead of Clayton™ HY.

These films were conditioned at 75° F./50% relative humidity. After conditioning 24 hours, the films were removed from conditioning and subjected to mechanical testing as described above. The results are set forth below in Table 5.

TABLE 5

Mechanical Properties of the Films of Examples 12-16

| Example | | Thickness (mil) | Peak Stress (MPa) | Peak Elongation (%) | Modulus (MPa) | Energy per Volume at Break (J/cm³) |
|---|---|---|---|---|---|---|
| 12 | MD | 1 | 60 ± 2 | 543 ± 4 | 184 ± 13 | 144 ± 3 |
|    | CD | 1 | 44 ± 3 | 859 ± 31 | 164 ± 2 | 170 ± 21 |
| 13 | MD | 1 | 52 ± 6 | 541 ± 67 | 147 ± 12 | 122 ± 21 |
|    | CD | 1 | 37 ± 3 | 826 ± 23 | 141 ± 11 | 138 ± 10 |
| 14 | MD | 1 | 31 ± 2 | 407 ± 19 | 105 ± 9 | 54 ± 3 |
|    | CD | 1 | 19 ± 2 | 756 ± 27 | 79 ± 11 | 65 ± 10 |
| 15 | MD | 1 | 55 ± 2 | 504 ± 15 | 178 ± 9 | 121 ± 8 |
|    | CD | 1 | 40 ± 2 | 846 ± 21 | 157 ± 7 | 164 ± 11 |
| 16 | MD | 1 | 20 ± 1 | 246 ± 20 | 68 ± 5 | 26 ± 2 |
|    | CD | 1 | 11 ± 2 | 673 ± 51 | 78 ± 6 | 44 ± 4 |

Example 17

A film layer was formed as described in Example 12, except that the target thickness was 12.7 micrometers and the screw speed was about 30 rpm.

Example 18

A film layer was formed as described in Example 13, except that the target thickness was 12.7 micrometers and the screw speed was about 30 rpm.

Example 19

A film layer was formed as described in Example 14, except that the target thickness was 12.7 micrometers and the screw speed was about 30 rpm.

Example 20

A film layer was formed as described in Example 15, except that the target thickness was 12.7 micrometers and the screw speed was about 30 rpm.

Example 21

A film layer was formed as described in Example 16, except that the target thickness was 12.7 micrometers and the screw speed was about 30 rpm.

These films were conditioned at 75° F./50% relative humidity. After conditioning 24 hours, the films were removed from conditioning and subjected to mechanical testing as described above. The results are set forth below in Table 6.

TABLE 6

Mechanical Properties of the Films of Examples 17-21

| Example | | Thickness (mil) | Peak Stress (MPa) | Peak Elongation (%) | Modulus (MPa) | Energy per Volume at Break (J/cm³) |
|---|---|---|---|---|---|---|
| 17 | MD | 0.5 | 71 ± 4 | 355 ± 29 | 250 ± 53 | 120 ± 5 |
|    | CD | 0.5 | 38 ± 2 | 832 ± 16 | 178 ± 11 | 156 ± 6 |
| 18 | MD | 0.5 | 56 ± 1 | 335 ± 39 | 176 ± 11 | 85 ± 7 |
|    | CD | 0.5 | 28 ± 2 | 790 ± 35 | 146 ± 19 | 99 ± 11 |
| 19 | MD | 0.5 | 37 ± 2 | 279 ± 24 | 163 ± 29 | 55 ± 3 |
|    | CD | 0.5 | 23 ± 0 | 737 ± 18 | 158 ± 9 | 94 ± 1 |
| 20 | MD | 0.5 | 68 ± 1 | 339 ± 16 | 237 ± 28 | 111 ± 6 |
|    | CD | 0.5 | 35 ± 2 | 824 ± 38 | 179 ± 21 | 152 ± 12 |
| 21 | MD | 0.5 | 23 ± 1 | 142 ± 5 | 145 ± 2 | 22 ± 3 |
|    | CD | 0.5 | 7 ± 1 | 538 ± 29 | 129 ± 9 | 26 ± 1 |

Control 3

A commercial film was tested that is produced by Quanxing Plastics, Inc. The film had a basis weight of 18 grams per square meters and was cast extruded from a blend containing 35 to 45 wt. % high density polyethylene (HDPE 5070), 20 to 30 wt. % low density polyethylene (LDPE LD100AC), 25 to 35 wt. % linear low density polyethylene (LLDPE 7050), and 5 to 10 wt. % of a titanium dioxide masterbatch (1605H). A micro-embossed pattern having a depth of 1 to 5 micrometers was formed on a surface of the film.

Example 22

A film was formed from a blend containing 93.5 wt. % of a polyethylene masterbatch, 4.5 wt. % of Clayton™ HY, and 2 wt. % of Fusabond® E-528, which is a graft copolymer of polyethylene and maleic anhydride available from DuPont. The polyethylene masterbatch contained 35 to 45 wt. % high density polyethylene (HDPE 5070), 20 to 30 wt. % low density polyethylene (LDPE LD100AC), 25 to 35 wt. % linear low density polyethylene (LLDPE 7050), and 5 to 10 wt. % of a titanium dioxide masterbatch (1605H). Clayton™ HY is an organoclay powder treated with quaternary ammonium solution and is available from BYK Additives, Inc. (Gonzales Tex.). The blend was formed using a co-rotating, twin screw extruder available from Entek®. The extruder had 14 processing barrels, with 13 heated barrels. Three barrels are open barrels. The outer diameter of the screws was 53 mm. The processing temperatures along the extruder were set as 175° C. and the compounding speed in the twin extruder was set as 700 rpm. The resultant strands were cooled in a water bath with 15 feet length in total. The cooled strand was then pelletized and collected for the following film processing.

A film was thereafter produced from the resulting blend using a single-screw extruder. The extruder has 8 processing barrels, with 7 heated barrels with temperatures ranging from 175-210° C. The screw speed was adjusted between 66.5 and 68.6 rpm depending on the required film thickness. The corresponding line speed was adjusted between 85 and 90 meters per minute. The resulting film had a basis weight of 13.5 grams per square meter. A micro-embossed pattern having a depth of 1 to 5 micrometers was formed on a surface of the film.

Example 23

A film was formed as described in Example 22, except that a deep embossing pattern having a depth of 5 to 15 micrometers was formed on the surface.

The films of Control 3, Example 22, and Example 23 were then tested for noise level as described herein. The tested films were rectangular and had a size of 13.5 centimeters by 28.0 centimeters. The results are shown in Table 7 below.

TABLE 7

Noise Level of Films at 4,000 Hz

| | Noise Level (dB) | Normalized Noise Level |
|---|---|---|
| Control 3 | 46.0 | 2.6 |
| Example 22 | 39.6 | 2.2 |
| Example 23 | 38.0 | 2.1 |
| Ambient | 17.7 | — |

As indicated above, the film of Examples 22 and 23 showed considerable reduction in noise level compared with the control sample.

Example 24

A film was formed from a blend containing 93.5 wt. % of a polyethylene masterbatch, 4.5 wt. % of Clayton™ HY, and 2 wt. % of Fusabond® E-528, which is a graft copolymer of polyethylene and maleic anhydride available from DuPont. The polyethylene masterbatch contained 25 to 35 wt. % high density polyethylene (HDPE 5070), 20 to 30 wt. % low density polyethylene (LDPE LD100AC), 15 to 25 wt. % linear low density polyethylene (LLDPE 7042), 15 to 25 wt. % linear low density polyethylene (LLDPE 7050), and 5 to 10 wt. % of a titanium dioxide masterbatch (1605H). The blend was formed using a co-rotating, twin screw extruder available from Entek®. The extruder had 14 processing barrels, with 13 heated barrels. Three barrels are open barrels. The outer diameter of the screws was 53 mm. The processing temperatures along the extruder were set as 175° C. and the compounding speed in the twin extruder was set as 700 rpm. The resultant strands were cooled in a water bath with 15 feet length in total. The cooled strand was then pelletized and collected for the following film processing.

A film was thereafter produced from the resulting blend using a single-screw extruder. The extruder has 8 processing barrels, with 7 heated barrels with temperatures ranging from 175-210° C. The screw speed was adjusted between 66.5 and 68.6 rpm depending on the required film thickness. The corresponding line speed was adjusted between 85 and 90 meters per minute. The resulting film had a basis weight of 17.0 grams per square meter. A micro-embossed pattern was also formed on the surface of the film that had a depth of 1-5 micrometers.

Example 25

A film was formed as described in Example 24, except that a deep embossing pattern having a depth of 5 to 15 micrometers was formed on the surface. The resulting film had a basis weight of 12.0 grams per square meter.

Control 4

An adult care absorbent article was produced on the commercial-scale equipment used to form DEPEND® products (Kimberly-Clark). The article contained a backsheet (thickness of 22.9 micrometers) cast extruded from a blend containing low density polyethylene (LDPE) and linear low density polyethylene (LLDPE). The article did not contain flaps.

Control 5

An adult care absorbent article was produced as described in Control 4, except that the article contained flaps.

Example 26

An adult care absorbent article (without flaps) was produced on the commercial-scale equipment used to form DEPEND® products (Kimberly-Clark). The article contained a backsheet (thickness of 12.7 micrometers) cast extruded from a blend containing 84.5 wt. % Dowlex™ EG 2047G, 4.5 wt. % of Clayton™ HY, 2.0 wt. % of Fusabond® E-528, and 9.0 wt. % Ampacet® 110313 (color additive, Ampacet Corporation). Dowlex™ EG 2047G is a linear low density polyethylene having a melt flow index of 2.3 g/10 minutes at 190° C. (Dow Chemical). The blend was formed using a co-rotating, twin screw extruder available from Entek. The extruder had 14 processing barrels, with 13 heated barrels. Three barrels are open barrels. The outer diameter of the screws was 53 mm. The processing temperatures along the extruder were set as 180° C. and the compounding speed in the twin extruder was set as 750 rpm. The resultant strands were cooled in a water bath with 20 feet length in total. The cooled strand was then pelletized and collected for the following film processing. The film was produced from the blend using a single-screw extruder. The screw had a diameter of 63.5 mm (L/D=30) and the screw speed was 86 rpm.

Example 27

An adult care absorbent article was formed as described in Example 26 except that it contained flaps.

The absorbent articles of Controls 3-4 and Examples 26-27 were then tested for noise level as described herein. A graphical depiction of the absorbent article of each of these examples is shown in FIG. 15, which shows the dimensions and the degree to which each side was laterally moved (i.e., 3.5 cm). The results are set forth in Table 8 below.

TABLE 8

| Noise Level of Articles at 2,000 Hz | | |
|---|---|---|
| | Noise Level (dB) | Normalized Noise Level |
| Control Example 2 | 32.6 | 1.62 |
| Control Example 3 | 31.3 | 1.56 |
| Example 5 | 29.1 | 1.44 |
| Example 6 | 27.9 | 1.39 |
| Ambient | 20.1 | — |

Example 28

A blown film was formed from a blend containing 84.5 wt. % Dowlex™ EG 2047G, 4.5 wt. % of Clayton™ HY, 2.0 wt. % of Fusabond® E-528, and 9.0 wt. % Ampacet® 110313 (color additive, Ampacet Corporation). The blend was formed using a co-rotating, twin screw extruder. The extruder had 14 processing barrels, with 13 heated barrels having a length of 210 mm. The outer diameter of the screws was 53 mm. The processing temperatures along the extruder were set as 180° C. and the compounding speed in the twin extruder was set as 750 rpm. The polyethylene was fed through one pellet feeder, the Fusabond® with Ampacet® additives were fed through another pellet feeder; and the nanoclay was fed through a powder throat feeder. The film was formed on a single screw extruder with a monolayer blown film die. The line speed was 175 pounds per hour and the thicknesses of films were controlled at 1.5 mils. The melt temperature was controlled within range of 175-185° C.

The oxygen transmission rate of the film was determined to be 277 $cm^3/in^2*24$ hours. A control sample containing only 95 wt. % Dowlex™ 2047 G with 5 wt. % Ampacet® was also formed. The oxygen transmission rate of the control film sample was determined to be 392 $cm^3/in^2*24$ hours.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article comprising:
    a liquid permeable layer;
    a generally liquid-impermeable layer that contains a film having a thickness of about 50 micrometers or less, wherein the film contains a layer that is formed from a polymer composition, the polymer composition containing
        an ethylene polymer that constitutes from about 75 wt. % to about 99 wt. % of the polymer composition,
        nanoclay having an organic surface treatment that constitutes from about 0.5 wt. % to about 20 wt. % of the polyer composition, and
        a polyolefin compatibilizer that contains an olefin component and a polar component that constitutes from about 0.1 wt. % to about 10 wt. % of the polymer composition,
        wherein the film exhibits a normalized Young's modulus, defined as the Young's modulus divided by an average film thickness in micrometers, in the machine direction and/or cross-machine direction of from about 5 to about 50 Megapascals per micrometer, an ultimate tensile strength in the machine direction and/or cross-machine direction of from about 20 to about 150 Megapascals;
        wherein the film exhibits a peak elongation in the machine direction of about 400% or more and/or a peak elongation in the cross-machine direction of about 750% or more, and
    an absorbent core positioned between the liquid permeable layer and the generally liquid-impermeable layer.

2. The absorbent article of claim 1, wherein the ethylene polymer is a copolymer of ethylene and an α-olefin.

3. The absorbent article of claim 2, wherein the ethylene polymer is linear low density polyethylene, low density polyethylene, or a combination thereof.

4. The absorbent article of claim 1, wherein the nanoclay includes a phyllosilicate.

5. The absorbent article of claim 4, wherein the phyllosilicate includes a montmorillonite or a salt thereof.

6. The absorbent article of claim 1, wherein the nanoclay includes platelets having an average thickness of from about 0.2 to about 100 nanometers.

7. The absorbent article of claim 1, wherein the polar component of the compatibilizer includes maleic anhydride.

8. The absorbent article of claim 1, wherein the ethylene polymer constitutes from about 80 wt. % to about 98 wt. % of the polymer composition and the compatibilizer constitutes from about 2 wt. % to about 8 wt. % of the composition.

9. The absorbent article of claim 1, wherein the film exhibits a peak elongation in the machine direction of about 500% or more and an ultimate tensile strength in the machine direction of from about 25 to about 100 Megapascals.

10. The absorbent article of claim 1, wherein the film exhibits a peak elongation in the cross-machine direction of about 800% or more and an ultimate tensile strength in the cross-machine direction of from about 25 to about 100 Megapascals.

11. The absorbent article of claim 1, wherein the film exhibits a Young's modulus in the machine direction and/or cross-machine direction of from about 100 to about 400 Megapascals.

12. The absorbent article of claim 11, wherein the backsheet further contains a nonwoven web laminated to the film.

13. The absorbent article of claim 1, wherein the generally liquid-impermeable layer is a backsheet of the absorbent article.

14. The absorbent article of claim 1, wherein the absorbent article exhibits a noise level of about 45 decibels or less when subjected to physical deformation for two minutes as determined at a frequency of 2,000 Hz.

15. A film having a thickness of about 50 micrometers or less, wherein the film contains a layer that is formed from a polymer composition, the polymer composition containing
    from about 75 wt. % to about 99 wt. % of an α-olefin/ethylene copolymer,
    from about 0.5 wt. % to about 20 wt. % of a nanoclay having an organic surface, and
    from about 0.1 wt. % to about 10 wt. % of a polyolefin compatibilizer that contains an olefin component and a polar component,
    wherein the film exhibits a peak elongation of about 450% or more in the machine direction and/or a peak elongation in the cross-machine direction of 750% or more; and ultimate tensile strength of from about 20 to about 150 MPa in the machine direction and/or cross-machine direction, and
    wherein the film exhibits a normalized Young's modulus, defined as the Young's modulus divided by an average film thickness in micrometers, in the machine direction and/or cross-machine direction of from about 5 to about 50 Megapascals per micrometer.

16. The film of claim 15, wherein the nanoclay includes a montmorillonite or a salt thereof.

17. The film of claim 15, wherein the nanoclay includes platelets having an average thickness of from about 0.2 to about 100 nanometers.

18. The film of claim 15, wherein the olefin component of the polyolefin compatibilizer comprises an ethylenically unsaturated carboxylic acid monomer that includes maleic anhydride.

19. The film of claim 15, wherein the film is multi-layered and contains a base layer and/or skin layer formed from the polymer composition.

20. The film of claim 15, wherein the film exhibits a Young's modulus in the machine direction and/or cross-machine direction of from about 50 to about 500 Megapascals.

21. The film of claim 15, wherein the film exhibits a noise level of about 45 decibels or less when subjected to physical deformation for two minutes as determined at a frequency of 4,000 Hz.

22. A method for forming the film of claim 15, the method comprising:
    forming a masterbatch by blending the ethylene polymer, nanoclay, and compatibilizer;
    melt processing the masterbatch to form the polymer composition; and
    applying the polymer composition to a surface to form the film.

23. The method of claim 22, wherein the masterbatch is formed in a twin screw extruder.

24. The method of claim 22, wherein the masterbatch is melt processed in a single screw extruder.

25. A method for forming the film of claim 15, the method comprising:
    melt processing an ethylene polymer, nanoclay, and compatibilizer to form a polymer composition; and
    applying the polymer composition to a surface to form the film.

26. The method of claim 25, wherein the nanoclay is in the form of a powder.

* * * * *